(12) United States Patent
McKillop et al.

(10) Patent No.: US 11,541,019 B2
(45) Date of Patent: Jan. 3, 2023

(54) COMPOSITIONS FOR USE IN THE TREATMENT OF DIABETES

(71) Applicant: University of Ulster, Coleraine (GB)

(72) Inventors: Aine Maire McKillop, Coleraine (GB); Peter Raymond Flatt, Coleraine (GB)

(73) Assignee: University of Ulster, County Londonderry (GB)

( * ) Notice: Subject to any disclaimer, the term of this patent is extended or adjusted under 35 U.S.C. 154(b) by 0 days.

(21) Appl. No.: 17/005,187

(22) Filed: Aug. 27, 2020

(65) Prior Publication Data

US 2021/0052515 A1 Feb. 25, 2021

Related U.S. Application Data

(63) Continuation of application No. 15/749,351, filed as application No. PCT/EP2016/068183 on Jul. 29, 2016, now abandoned.

(30) Foreign Application Priority Data

Jul. 31, 2015 (GB) ...................................... 1513543

(51) Int. Cl.

| | | |
|---|---|---|
| *A61K 31/122* | (2006.01) | |
| *A61K 31/7004* | (2006.01) | |
| *A61K 31/405* | (2006.01) | |
| *A61P 3/04* | (2006.01) | |
| *A61P 3/10* | (2006.01) | |

(52) U.S. Cl.
CPC .......... *A61K 31/122* (2013.01); *A61K 31/405* (2013.01); *A61K 31/7004* (2013.01); *A61P 3/04* (2018.01); *A61P 3/10* (2018.01); *A61K 2300/00* (2013.01)

(58) Field of Classification Search
CPC ................ A61K 31/122; A61K 31/405; A61K 31/7004; A61K 2300/00; A61P 3/04; A61P 3/10
USPC .......................................................... 514/23
See application file for complete search history.

(56) References Cited

FOREIGN PATENT DOCUMENTS

| CN | 102327262 | 1/2012 |
| KR | 20100070664 | 6/2010 |
| KR | 20150069105 | 6/2015 |

OTHER PUBLICATIONS

Gupta et al. Antioxidant activity and protection of pancreatic b-cells by embelin in streptozotocin-induced diabetes. Journal of Diabetes 4 (2012) 248-256. (Year: 2012).*
Chaudhari et al. Preventive Effect of Embelin from Embelia ribes on Lipid Metabolism and Oxidative Stress in High-Fat Diet-Induced Obesity in Rats. Planta Med 2012; 78: 651-657. (Year: 2012).*
Sun et al. Elevated cell proliferation and VEGF production by high-glucose. Eye (2013) 27, 1299-1307. (Year: 2013).*
Head et al. Connexin-36 Gap Junctions Regulate In Vivo First- and Second-Phase Insulin Secretion Dynamics and Glucose Tolerance in the Conscious Mouse. Diabetes 61:1700-1707, 2012. (Year: 2012).*
Gandhi, et al., "Insulin sensitization via partial antagonism of PPARγ and glycose uptake through translocation and activation of GLUT4 in PI3K/p-Akt signaling pathway by embelin in type 2 diabetic rats", Biochim Biophys Acta;Jan. 2013;1830(1):2243-2255.
Gupta, et al., "Antioxidant activity and protection of pancreatic p-cells by embelin in streptozotocin-induced diabetes", J Diabetes;Sep. 2012;4(3):248-256.
Naik, et al., "Anti-diabetic activity of embelin: involvement of cellular inflammatory mediators, oxidative stress and other biomarkers", Phytomedicine; Jul. 2013;20(10):797-804.
International Search Report and Written in Opinion in corresponding PCT/EP2016/068183, dated Dec. 2, 2016.
Office Action in corresponding U.S. Appl. No. 15/749,351, dated Dec. 10, 2018.
Office Action in corresponding U.S. Appl. No. 15/749,351, dated Jul. 29, 2019.
Chaudhari, et al., "Preventive Effect of Embelin from Embelia ribes on Lipid Metabolism and Oxidative Stress in High-Fat Diet-Induced Obesity in Rats", Planta Med;2012;78;651-657.
Sun, et al., "Elevated cell proliferation and VEGF production by high-glucose" Eye;2013;27; 1299-1307.
Head, et al., "Connexin-36 Gap Junctions Regulate in Vivo First- and Second-Phase Insulin Secretion Dynamics and Glucose Tolerance in the Conscious Mouse", Diabetes;2012;61;1700-1707.

* cited by examiner

*Primary Examiner* — Yih-Horng Shiao
(74) *Attorney, Agent, or Firm* — Hovey Williams LLP

(57) ABSTRACT

This invention relates to compositions for use in the treatment of diabetes, for example type-2 diabetes; obesity; and/or metabolic syndrome. Specifically, the invention relates to a composition for use in the treatment of diabetes, the composition comprising at least one of diindolylmethane; indole-3-carbinol; embelin; [6]-gingerol; and [6]-shogaol, or combinations each thereof. Also disclosed is use in the treatment of obesity and use in the treatment of metabolic syndrome.

10 Claims, 30 Drawing Sheets

Figure 1: Double immunofluorescence of GPR-a1 merge with insulin in clonal pancreatic BRIN-BD11 cells.
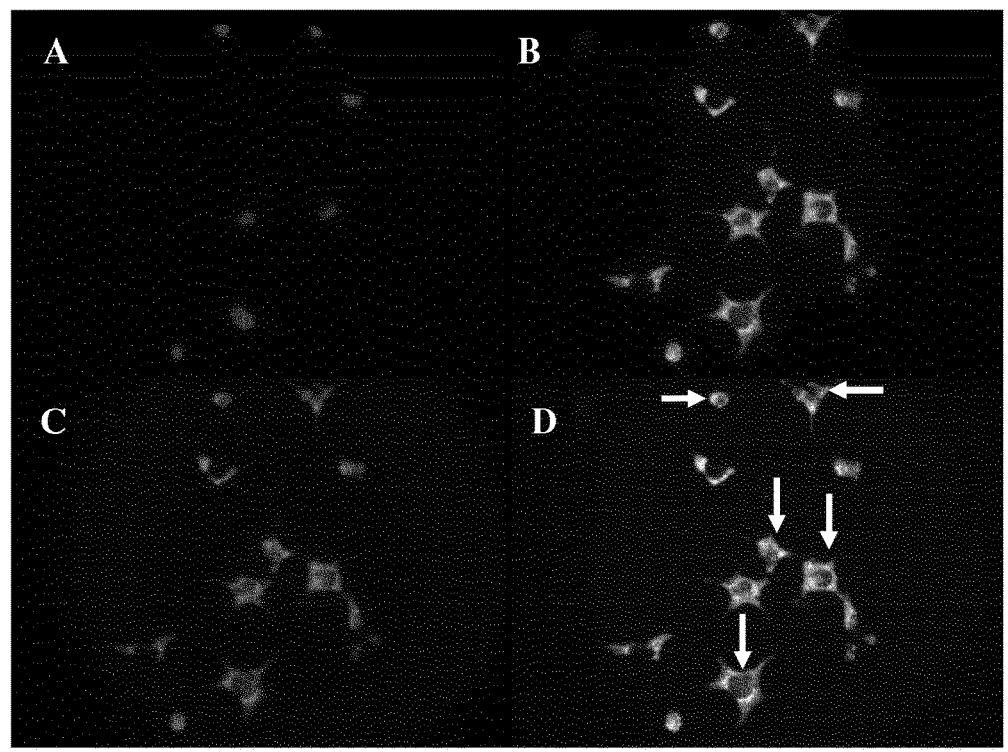
Distribution of (A) DAPI, (B) insulin (C) GPR-a1 (D) merge of GPR-a1 colocalised with insulin at x40 magnification in clonal BRIN-BD11 cells. Examples of co-localisation are indicated by the arrows.

Figure 2: Cellular localisation of GPR-a1 with insulin and glucagon in mouse pancreatic tissue.
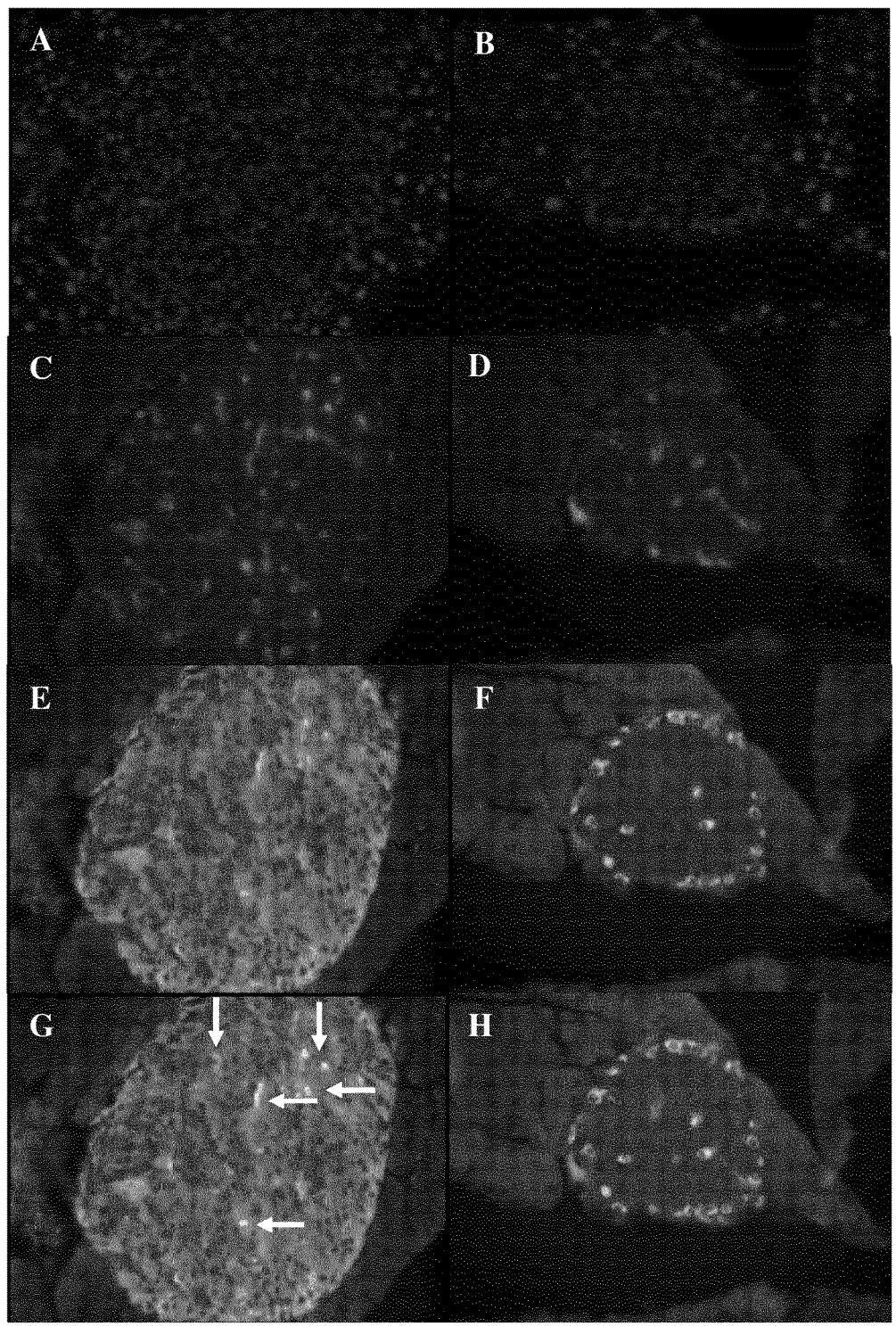
Distribution of (A, B) DAPI, (C,D) GPR-a1 (E) insulin (F) glucagon (G) merge of GPR-a1 colocalised with insulin (H) merge of GPR-a1 with glucagon at x40 magnification in lean mouse tissue. Examples of co-localisation are indicated by the arrows.

Figure 3: Effect of Agonist-1 on insulin secretion and LDH release from clonal BRIN-BD11 cells at 5.6mM glucose.
A
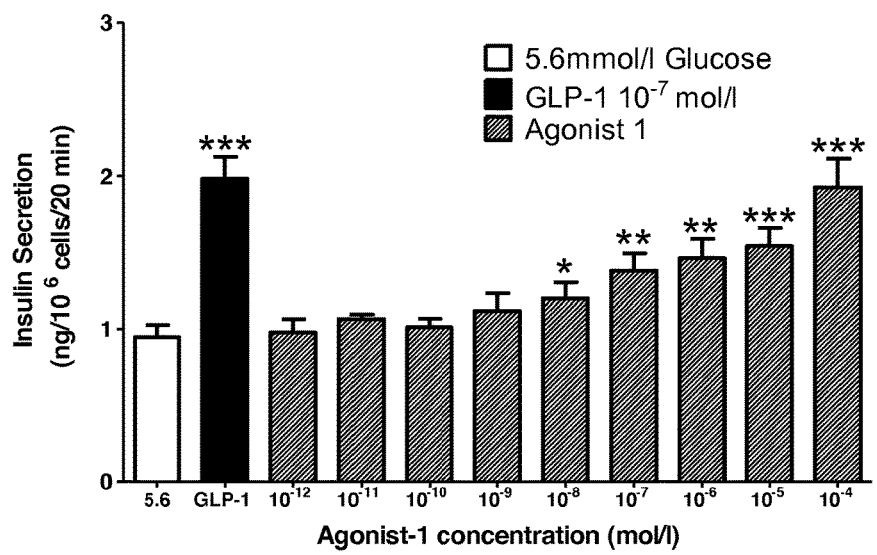
B
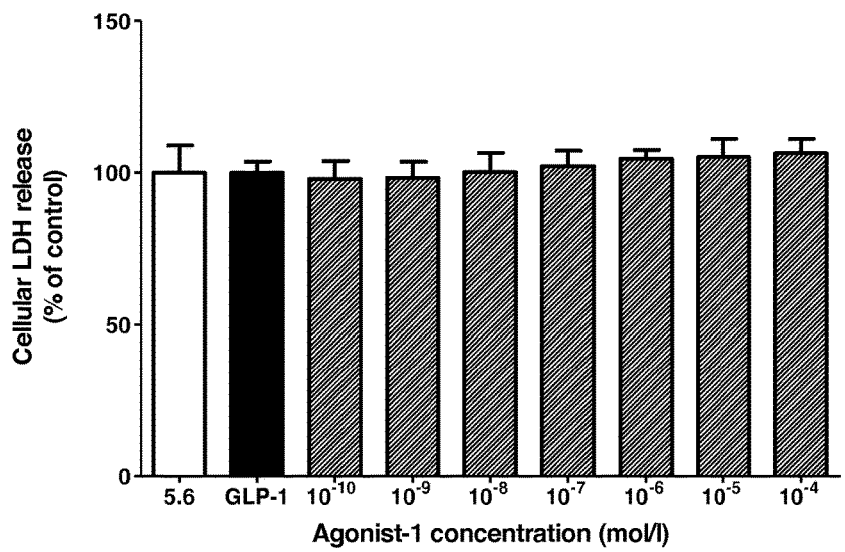
Effect of Agonist-1 ($10^{-12}$-$10^{-4}$ M) and GLP-1 ($10^{-7}$ M) on (A) insulin secretion and (B) LDH release from clonal BRIN-BD11 cells at 5.6mM glucose. Results are the mean ± SEM (n=8) for insulin secretion and (n=4) for LDH release. * $p<0.05$,  $p<0.01$, * $p<0.001$ compared to glucose alone.

Figure 4: Effect of Agonist-1 on insulin secretion and LDH release from clonal BRIN-BD11 cells at 16.7mM glucose.
A
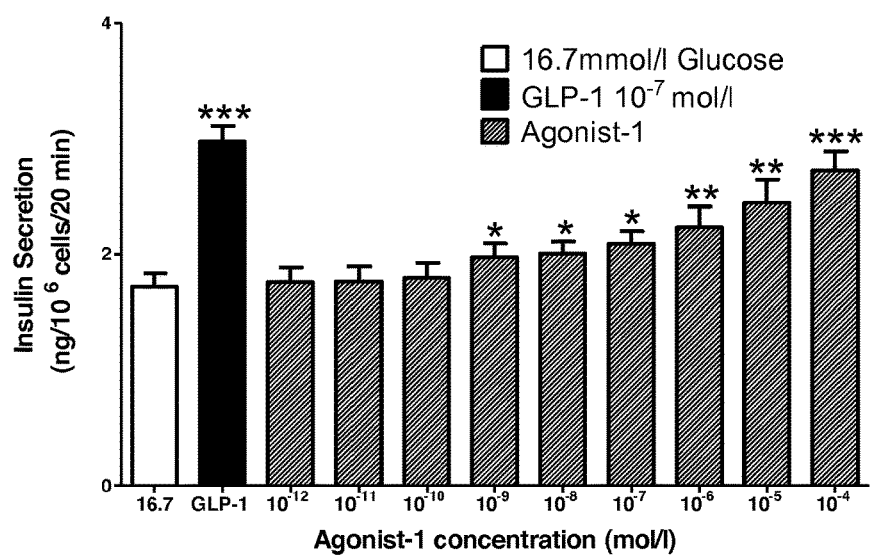
B
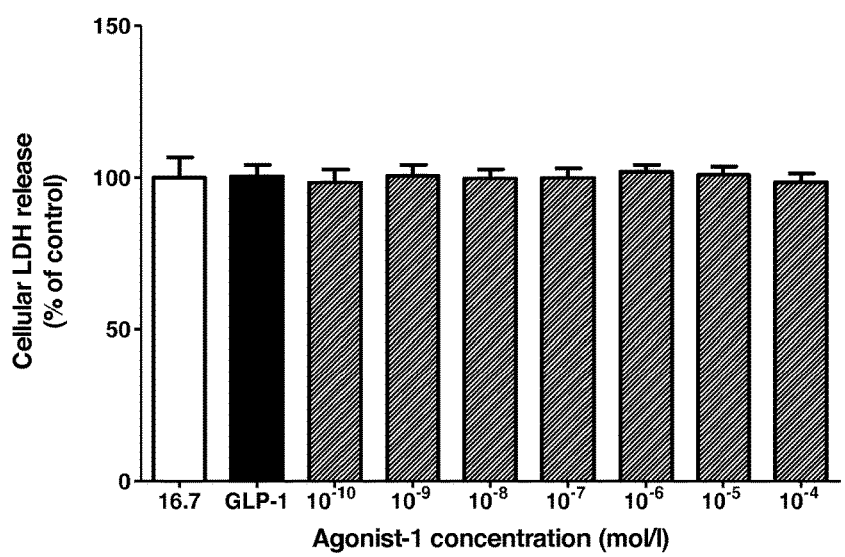
Effect of Agonist-1 ($10^{-12}$-$10^{-4}$ M) and GLP-1 ($10^{-7}$ M) on (A) insulin secretion and (B) LDH release from clonal BRIN-BD11 cells at 16.7mM glucose. Results are the mean ± SEM (n=8) for insulin secretion and (n=4) for LDH release. * $p<0.05$,  $p<0.01$, * $p<0.001$ compared to glucose alone.

Figure 5: Effect of Agonist-3 on insulin secretion and LDH release from clonal BRIN-BD11 cells at 5.6mM glucose.
A
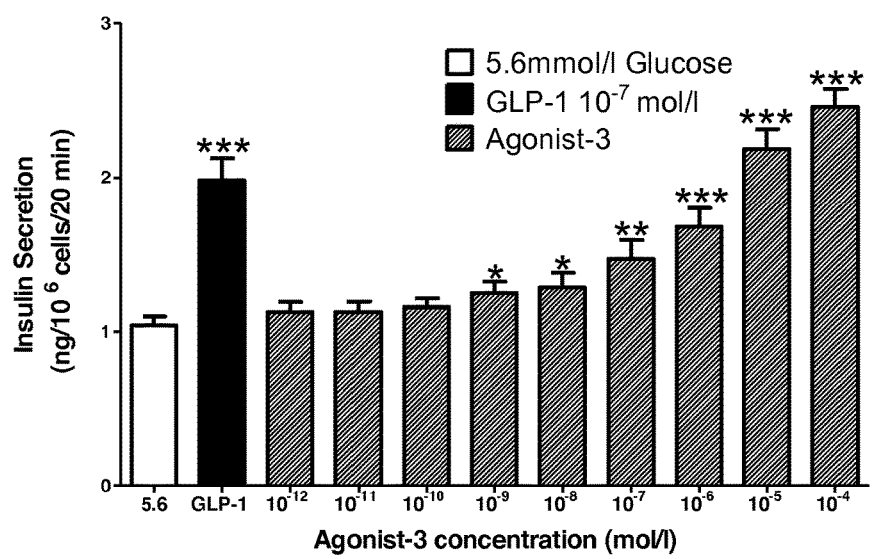
B
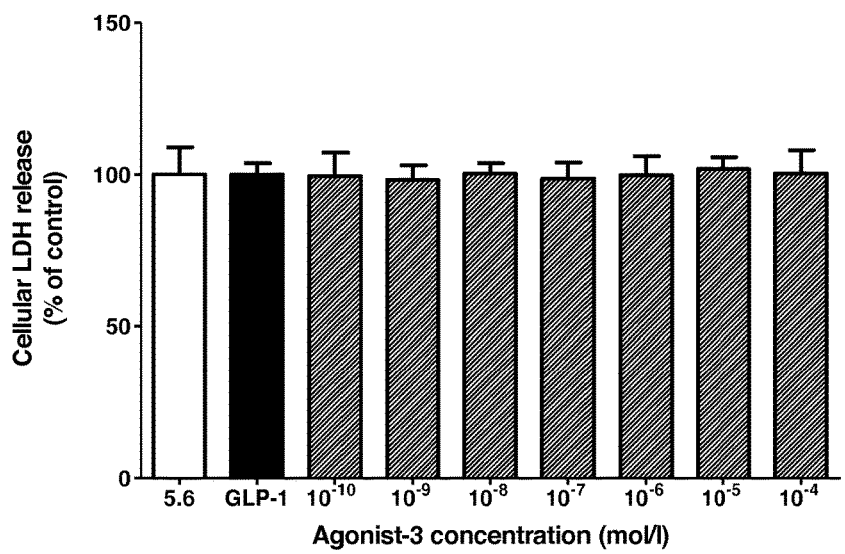
Effect of Agonist-3 ($10^{-12}$-$10^{-4}$ M) and GLP-1 ($10^{-7}$ M) on (A) insulin secretion and (B) LDH release from clonal BRIN-BD11 cells at 5.6mM glucose. Results are the mean ± SEM (n=8) for insulin secretion and (n=4) for LDH release. * $p<0.05$,  $p<0.01$, * $p<0.001$ compared to glucose alone.

Figure 6: Effect of Agonist-3 on insulin secretion and LDH release from clonal BRIN-BD11 cells at 16.7mM glucose.
A
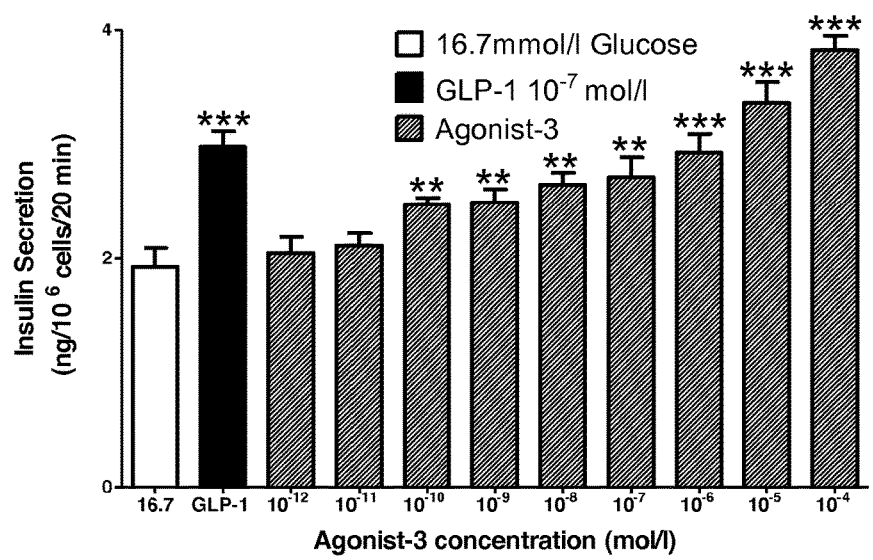
B
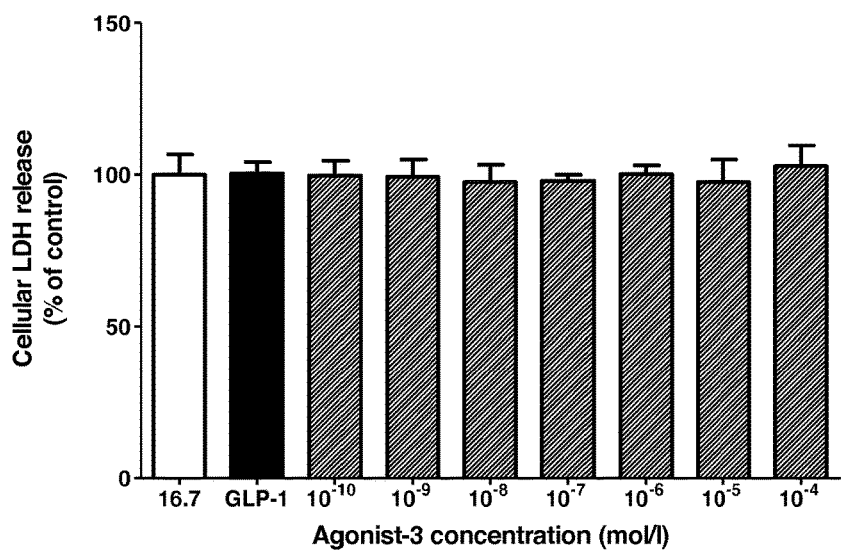
Effect of Agonist-3 ($10^{-12}$-$10^{-4}$ M) and GLP-1 ($10^{-7}$ M) on (A) insulin secretion and (B) LDH release from clonal BRIN-BD11 cells at 16.7mM glucose. Results are the mean ± SEM (n=8) for insulin secretion and (n=4) for LDH release.  $p<0.01$, * $p<0.001$ compared to glucose alone.

Figure 7: Effect of GPR-a1 agonists and alanine on intracellular $Ca^{2+}$ from clonal BRIN-BD11 cells at 5.6mM glucose.
A
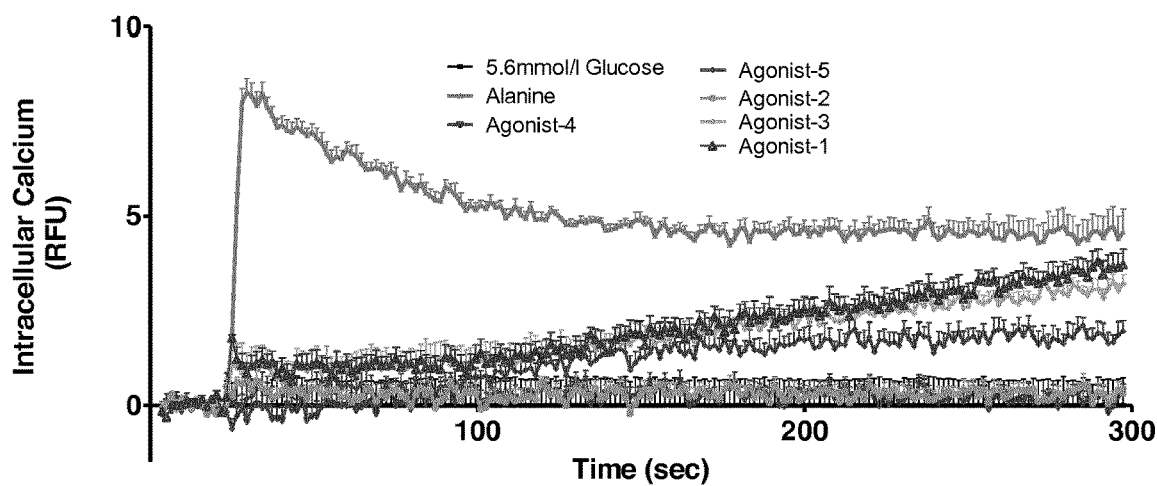
B
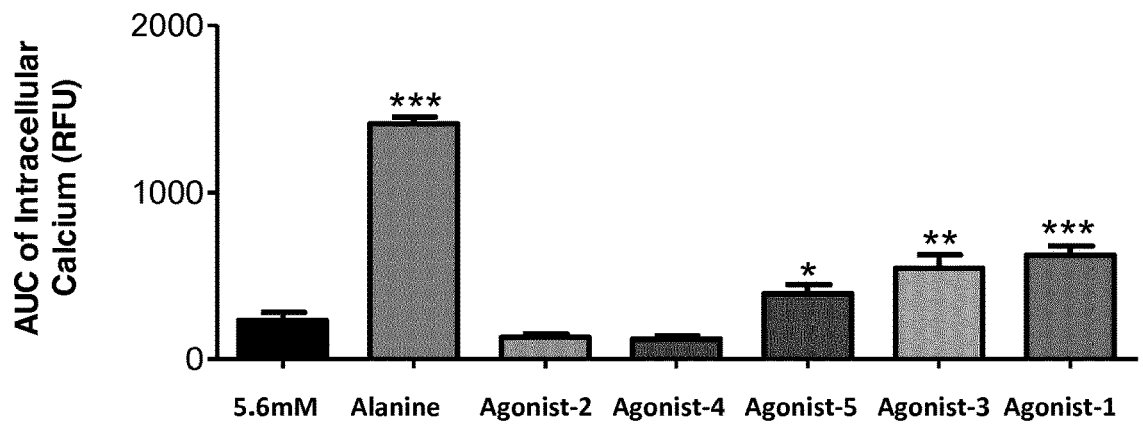
Exposure of BRIN-BD11 cells to alanine (10mM), Agonist-1, -2, -3, -4, -5 ($10^{-4}$ M) at 5.6mM glucose with (A) intracellular $Ca^{2+}$ measurements (RFU) for 5 min and (B) corresponding AUC graph. Results are the mean ± SEM (n=8). * $p<0.05$,  $p<0.01$ and * $p<0.001$ compared to the glucose control.

Figure 8: Effect of medium chain fatty acids and alanine on intracellular $Ca^{2+}$ from clonal BRIN-BD11 cells at 5.6mM glucose.
A
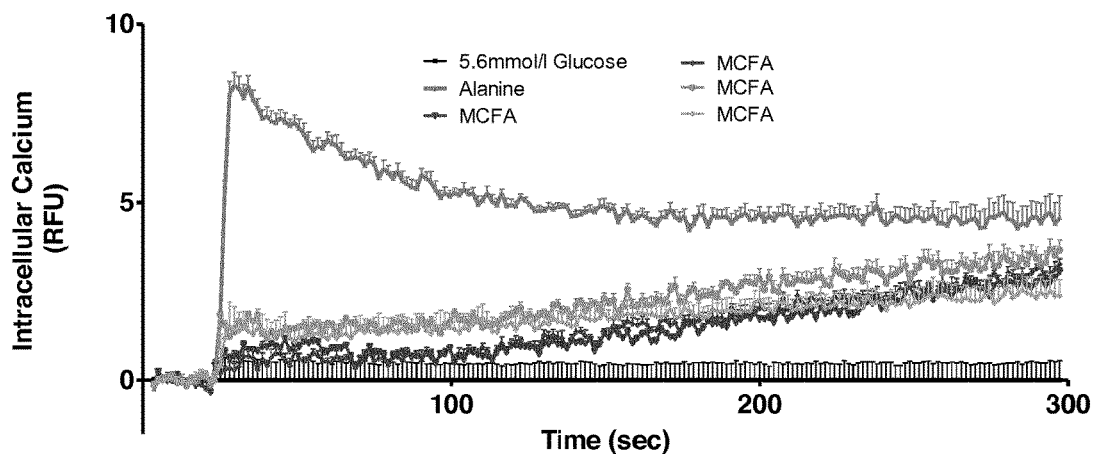
B
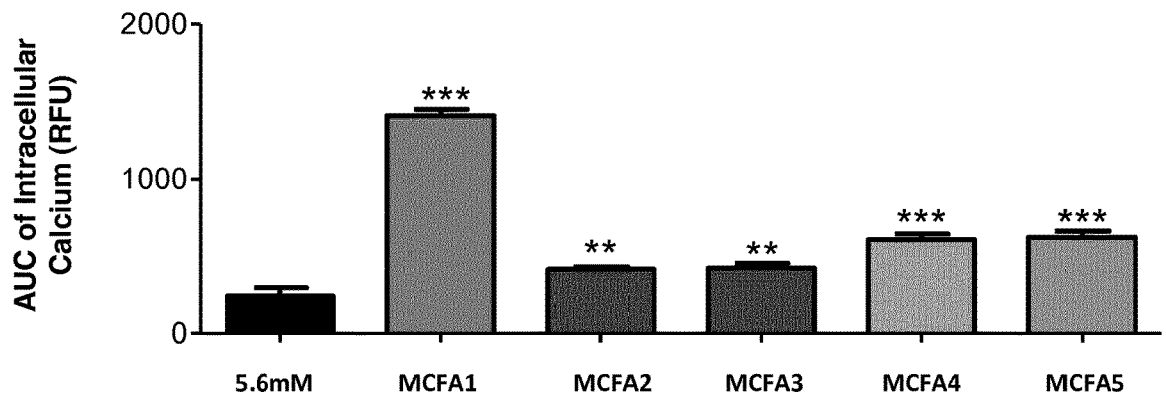
Exposure of BRIN-BD11 cells to alanine (10mM), and MCFAs ($10^{-4}$ M) at 5.6mM glucose with (A) intracellular $Ca^{2+}$ measurements (RFU) for 5 min and (B) corresponding AUC graph. Results are the mean ± SEM (n=8).  $p<0.01$ and * $p<0.001$ compared to the glucose control.

Figure 9: Effect of medium chain fatty acids and alanine on intracellular $Ca^{2+}$ from clonal BRIN-BD11 cells at 16.7mM glucose.
A
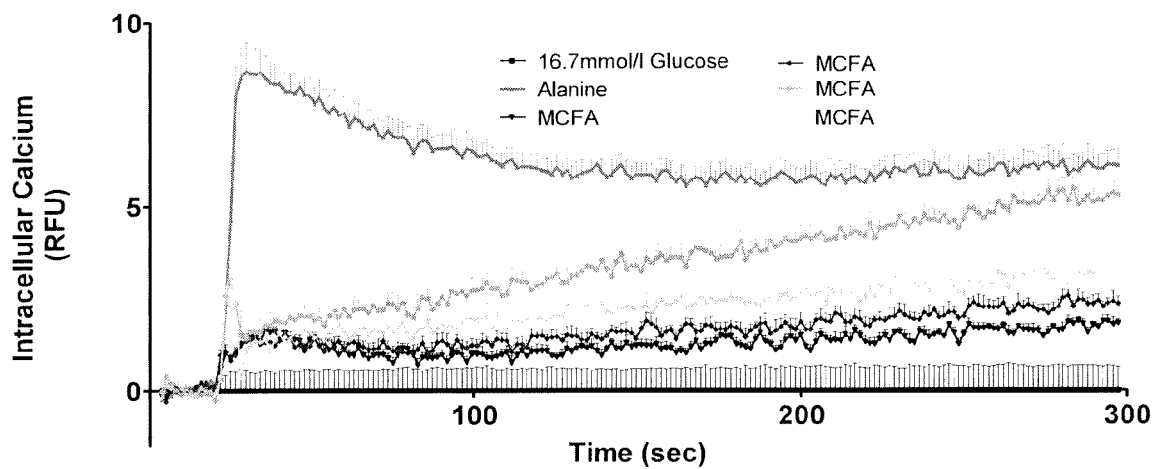
B
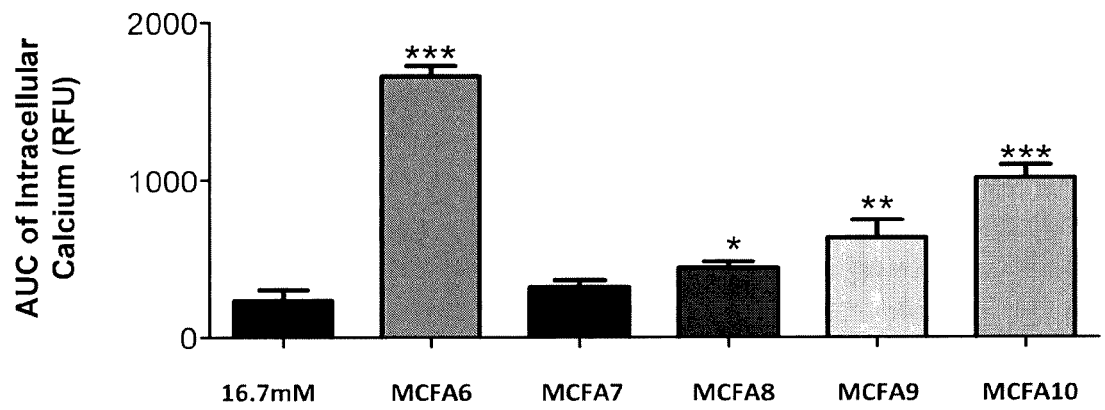
Exposure of BRIN-BD11 cells to alanine (10mM), MCFAs ($10^{-4}$ M) at 16.7mM glucose with (A) intracellular $Ca^{2+}$ measurements (RFU) for 5 min and (B) corresponding AUC graph. Results are the mean ± SEM (n=8). * $p<0.05$,  $p<0.01$ and * $p<0.001$ compared to the glucose control.

Figure 10: Effect of alternative GPR-a1 agonists and alanine on intracellular $Ca^{2+}$ from clonal BRIN-BD11 cells at 16.7mM glucose.
A
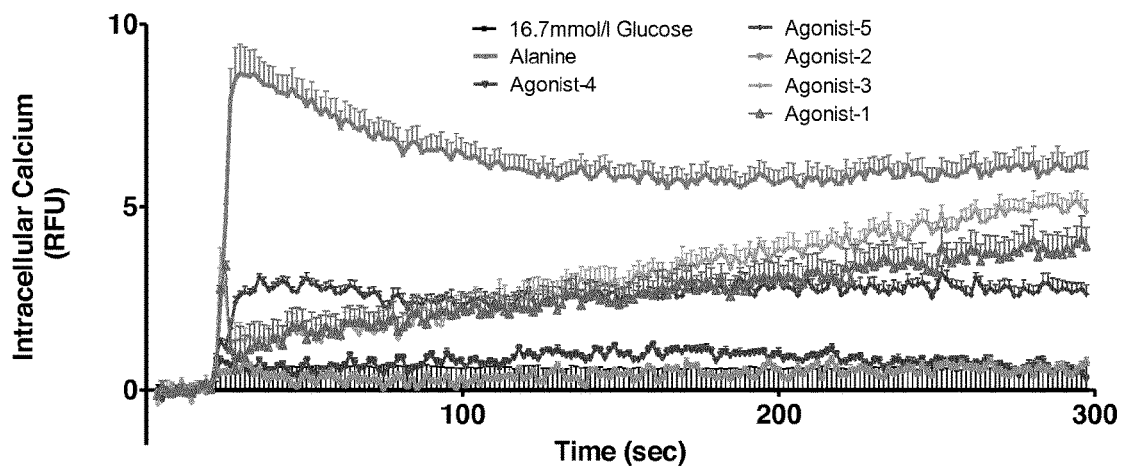
B
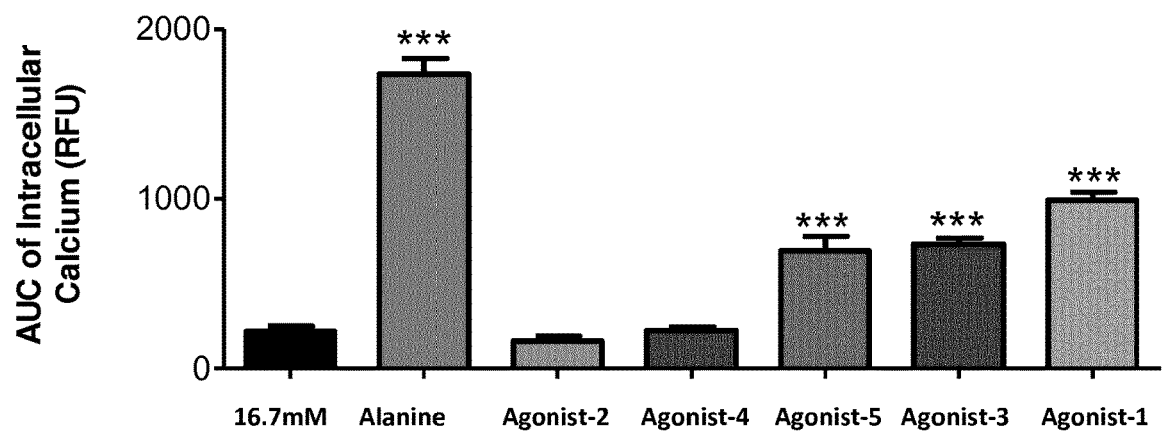
Exposure of BRIN-BD11 cells to alanine (10mM), Agonist-1, -2, -3, -4, -5 ($10^{-4}$ M) at 16.7mM glucose with (A) intracellular $Ca^{2+}$ measurements (RFU) for 5 min and (B) corresponding AUC graph. Results are the mean ± SEM (n=8). *** $p<0.001$ compared to the glucose control.

Figure 11: Effect of alternative GPR-a1 agonists and GLP-1 on cAMP production from clonal BRIN-BD11 cells at 11.1mM glucose.
A
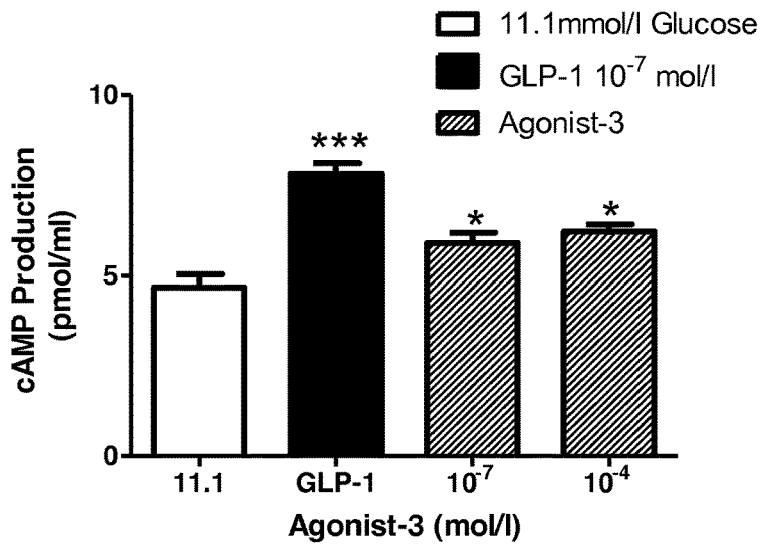
B
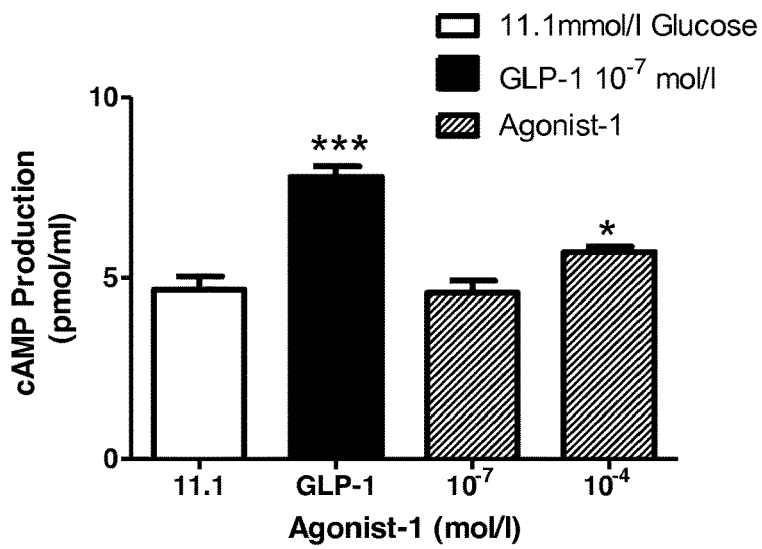
Effect of (A) Agonist-3 (B) Agonist-1 ($10^{-7}$-$10^{-4}$ M) and GLP-1 ($10^{-7}$ M) on cAMP production in BRIN-BD11 cells at 11.1mM glucose. Results are the mean ± SEM (n=3). * $p<0.05$ and *** $p<0.001$ compared to the glucose control.

Figure 12: Acute effects of alternative GPR-a1 agonists on plasma glucose in NIH Swiss mice on normal chow and high fat diet following glucose load.
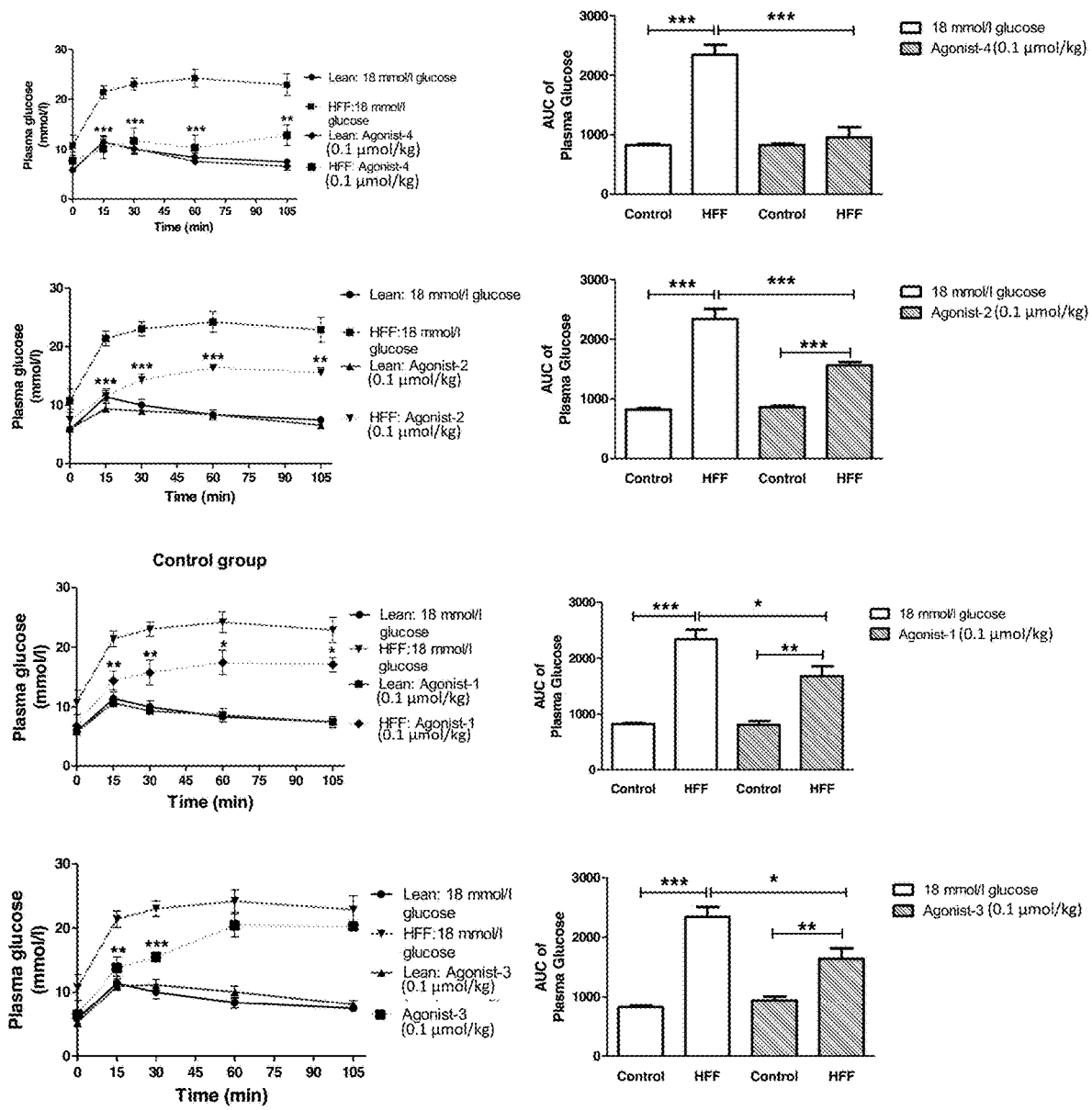
Effects of GPR-a1 agonists (0.1 μmol/kg) on plasma glucose and AUC of plasma glucose in control and HFF NIH Swiss mice. Results are the mean ± SEM (n=6) *p<0.05, p<0.01, *p<0.001 compared to control.

Figure 13: Acute effects of medium chain fatty acids on plasma glucose in NIH Swiss mice on normal chow and high fat diet following glucose load.
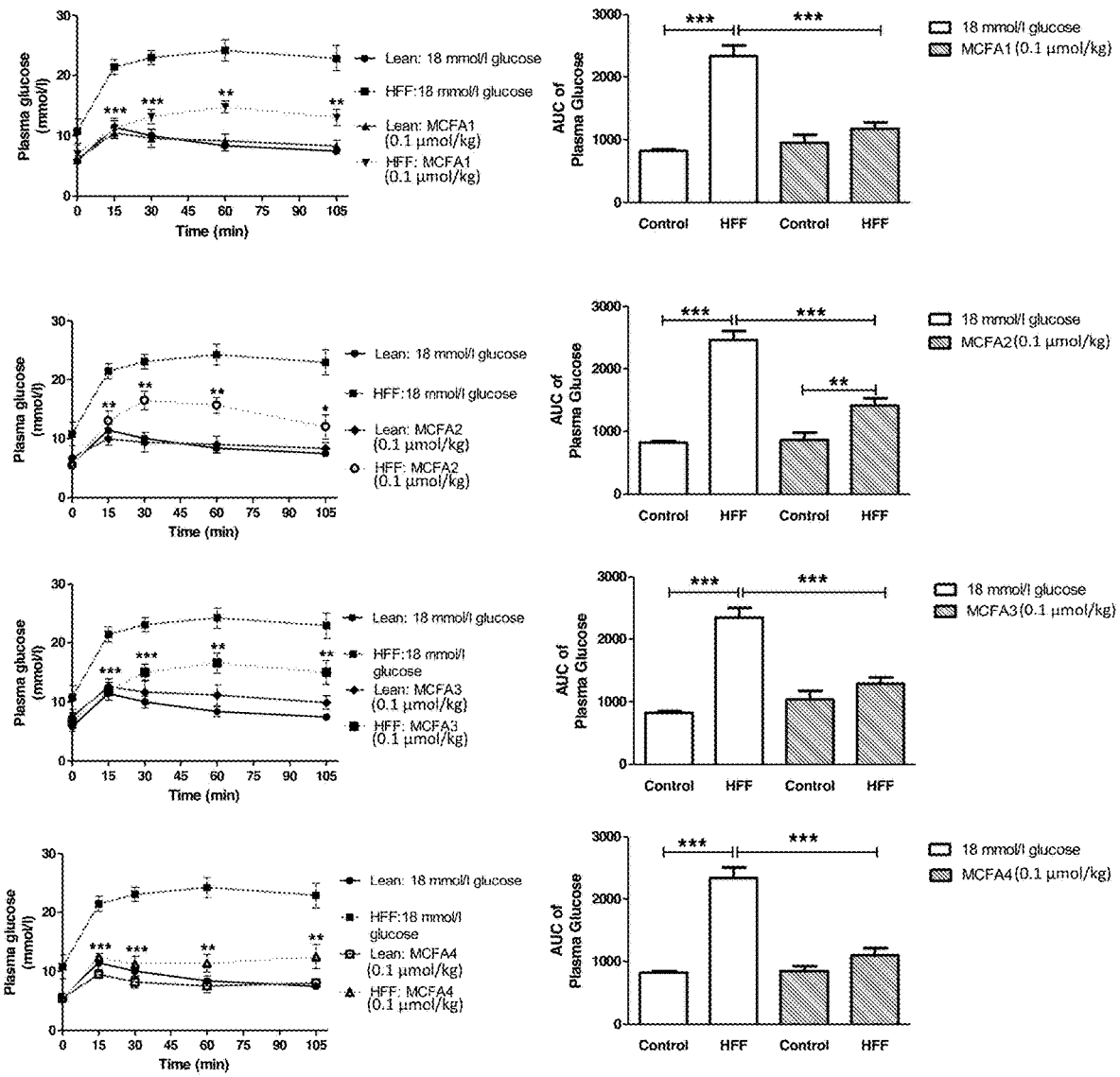
Effects of GPR-a1 agonists (0.1 μmol/kg) on plasma glucose and AUC of plasma glucose in control and HFF NIH Swiss mice. Results are the mean ± SEM (n=6) *p<0.05, p<0.01, *p<0.001 compared to control.

Figure 14: Acute effects of GPR-a1 agonists on plasma glucose and plasma insulin in NIH Swiss mice on normal chow and high fat diet following glucose load.
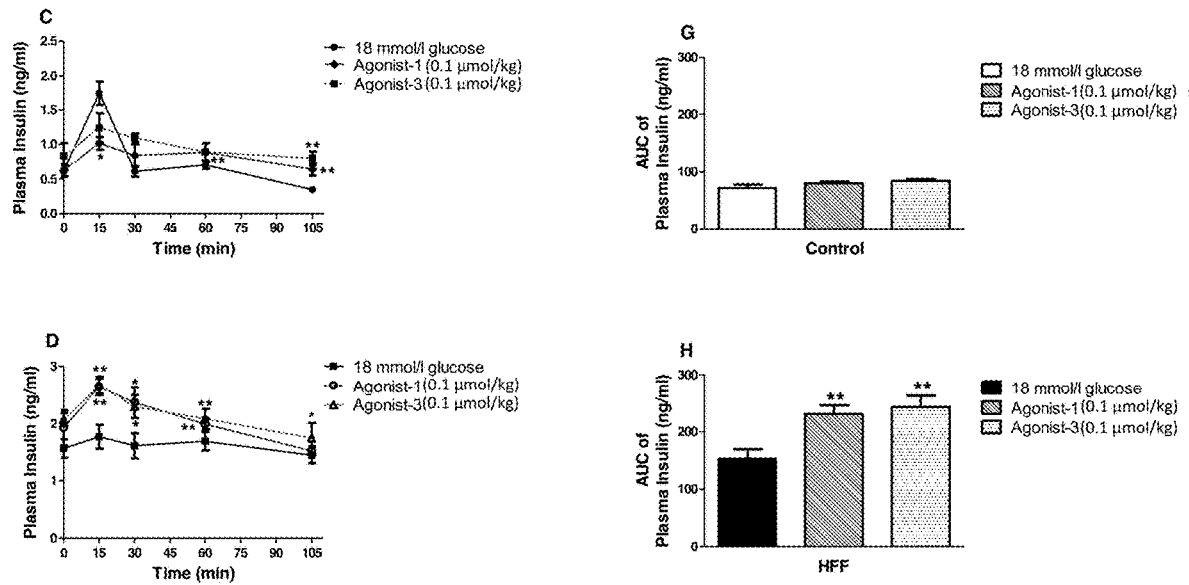
Effects of Agonist-1 and Agonist-3 on plasma insulin (C, D) and AUC of plasma insulin (G,H) in control and HFF NIH Swiss mice. Results are the mean ± SEM (n=6) *$p<0.05$ and **$p<0.01$ compared to control.

Figure 15: Effects of daily administration of (A) Agonist-3 and (B) Agonist-1 on non-fasting blood glucose in mice fed on a high-fat diet
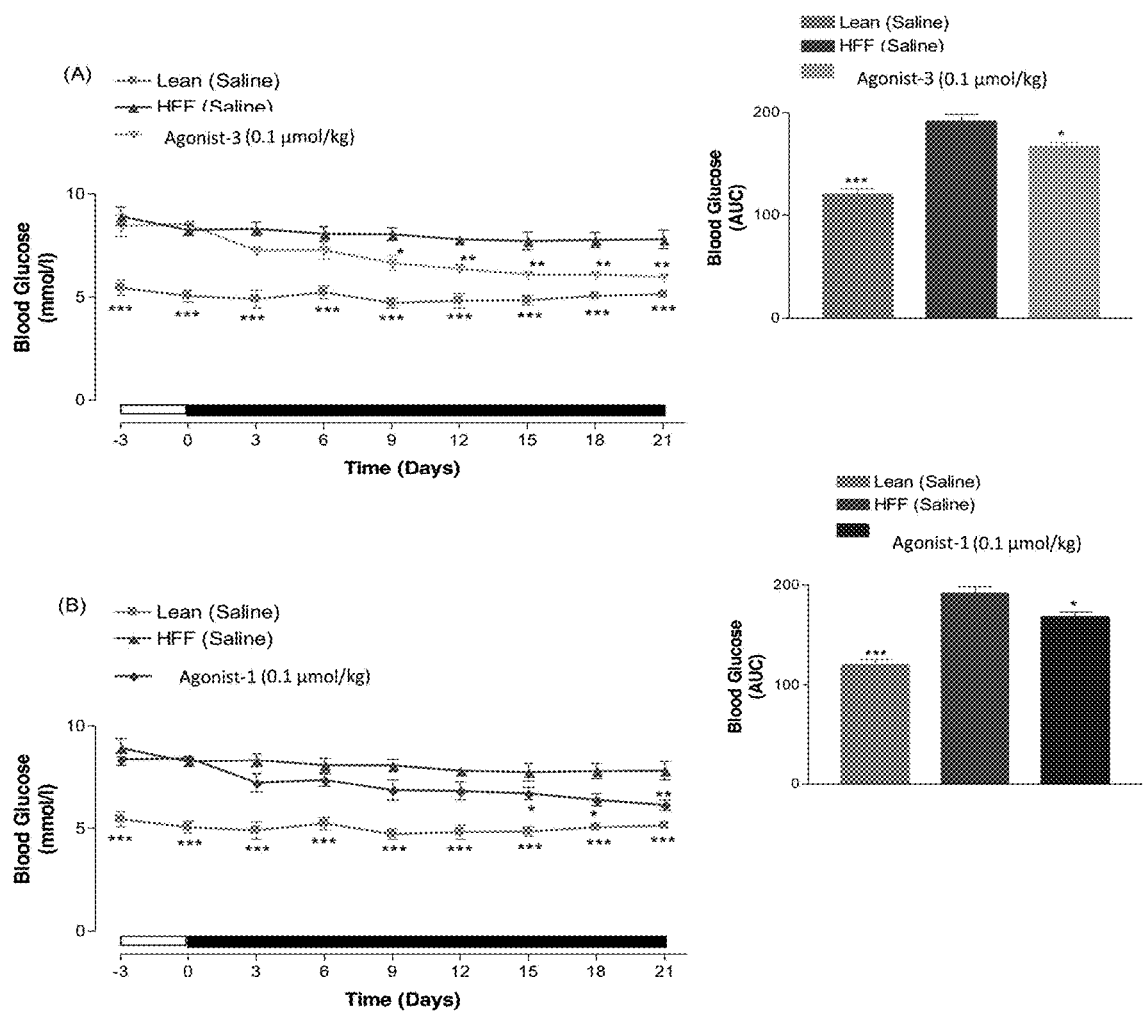
Blood glucose was measured every 3 days throughout the experiment. Values are Mean ± SEM for 6 mice. * $P < 0.05$,  $P < 0.01$ and * $P < 0.001$ compared to high-fat fed control.

Figure 16: Effects of daily administration of (A) Agonist-3 and (B) Agonist-1 on non-fasting plasma insulin in mice fed on a high-fat diet
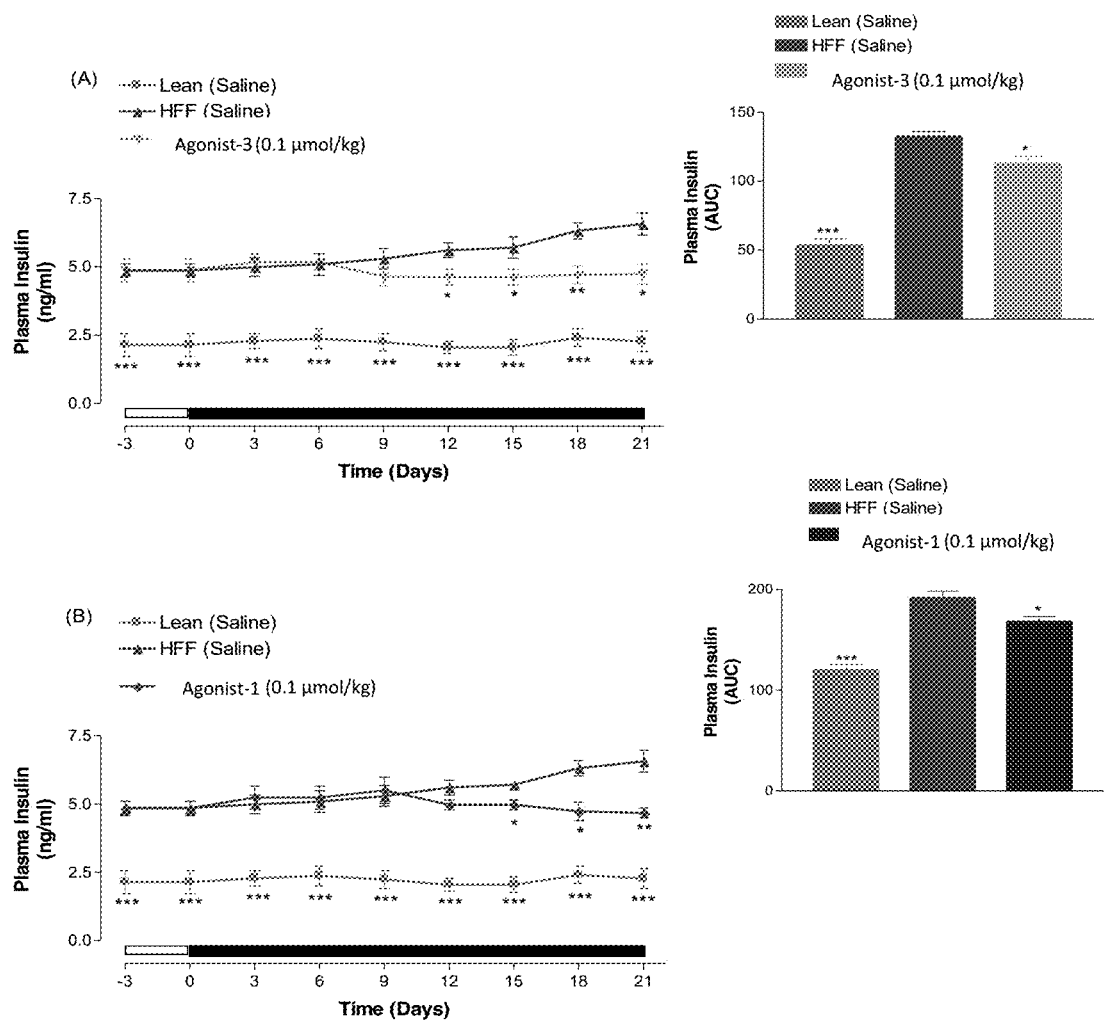
Plasma insulin was measured every 3 days throughout the experiment. Values are Mean ± SEM for 6 mice. * $P < 0.05$,  $P < 0.01$ and * $P < 0.001$ compared to high-fat fed control.

Figure 17: Effects of daily administration of (A) Agonist 3 and (B) Agonist-1 on body weight in mice fed on a high-fat diet
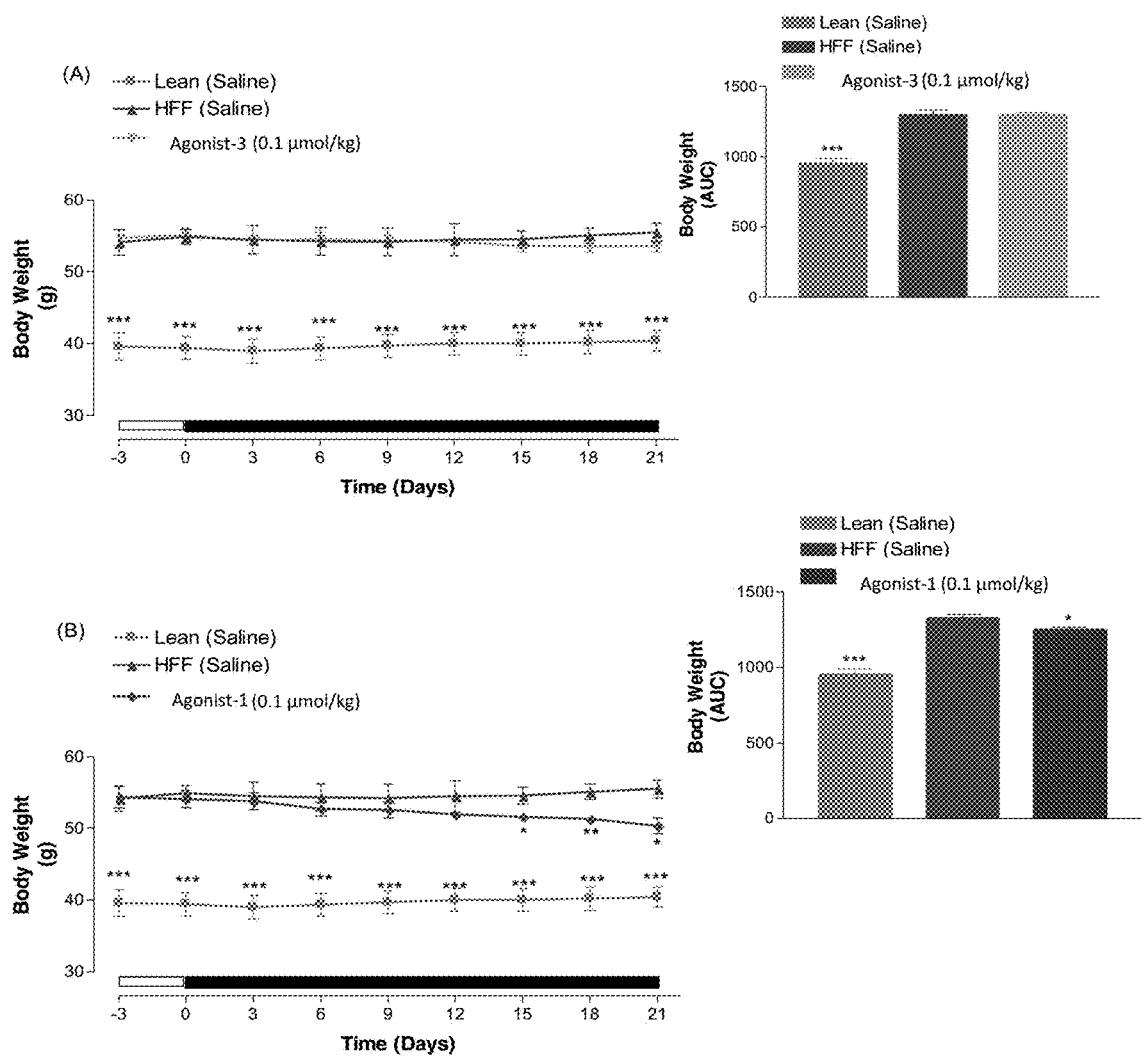
Body weight was measured every 3 days throughout the experiment. Values are Mean ± SEM for 6 mice. * P < 0.05,  P < 0.01 and * P < 0.001 compared to high-fat fed control.

Figure 18: Effects of daily administration of (A) Agonist-3 and (B) Agonist-1 on energy intake in mice fed on a high-fat diet
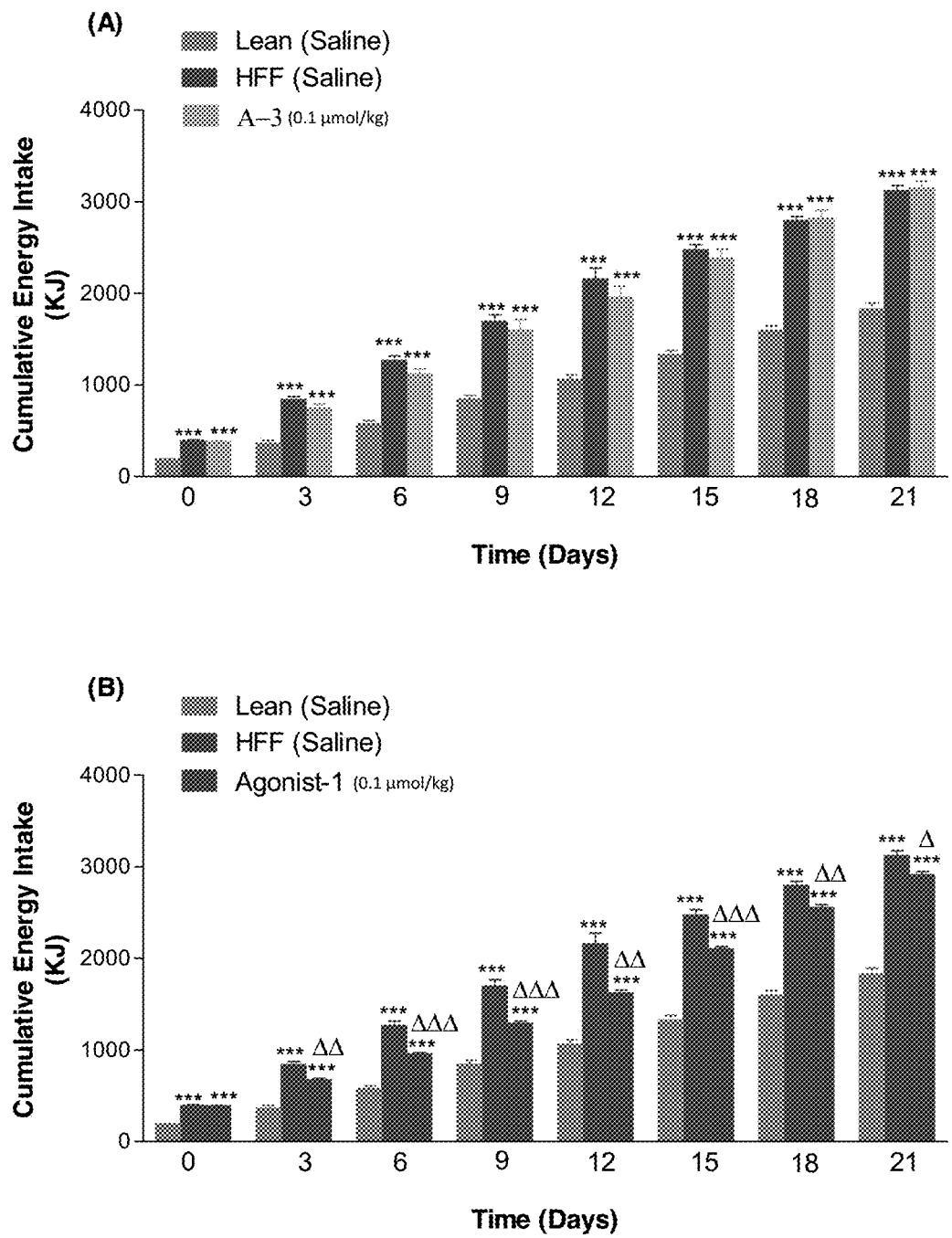
Energy intake was measured every 3 days throughout the experiment. Values are Mean ± SEM for 6 mice. *** $P < 0.001$ compared to lean control. $^\Delta$ $P < 0.05$, $^{\Delta\Delta}$ $P < 0.01$ and $^{\Delta\Delta\Delta}$ $P < 0.001$ compared to high-fat fed control.

Figure 19: Effects of daily administration of (A) Agonist-3 and (B) Agonist-1 on fluid intake in mice fed on a high-fat diet
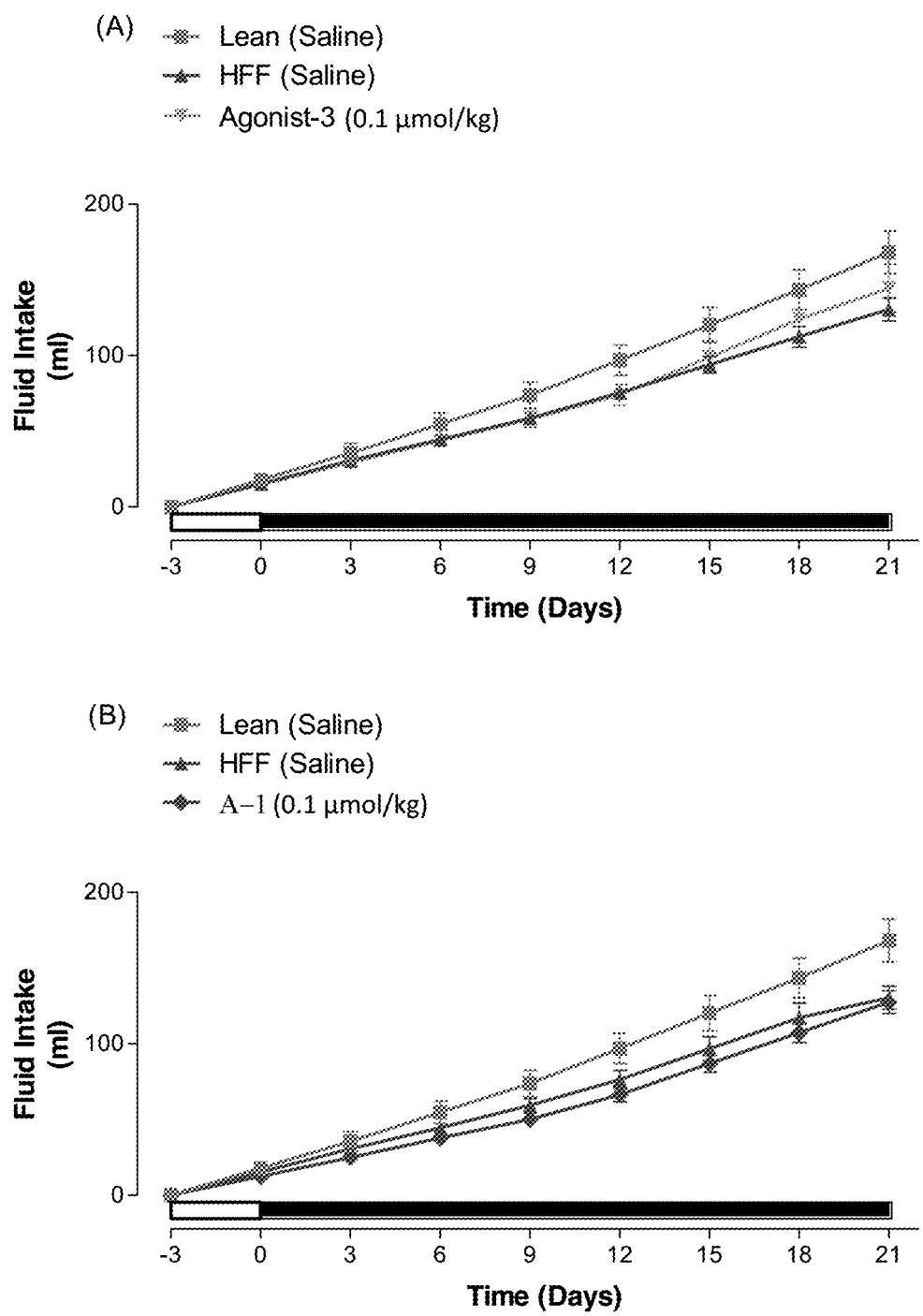
Fluid intake was measured every 3 days throughout the experiment. Values are Mean ± SEM for 6 mice.

Figure 20: Effects of daily administration of (A) Agonist-3 and (B) Agonist-1 on blood glucose following oral administration of glucose to mice fed on a high-fat diet

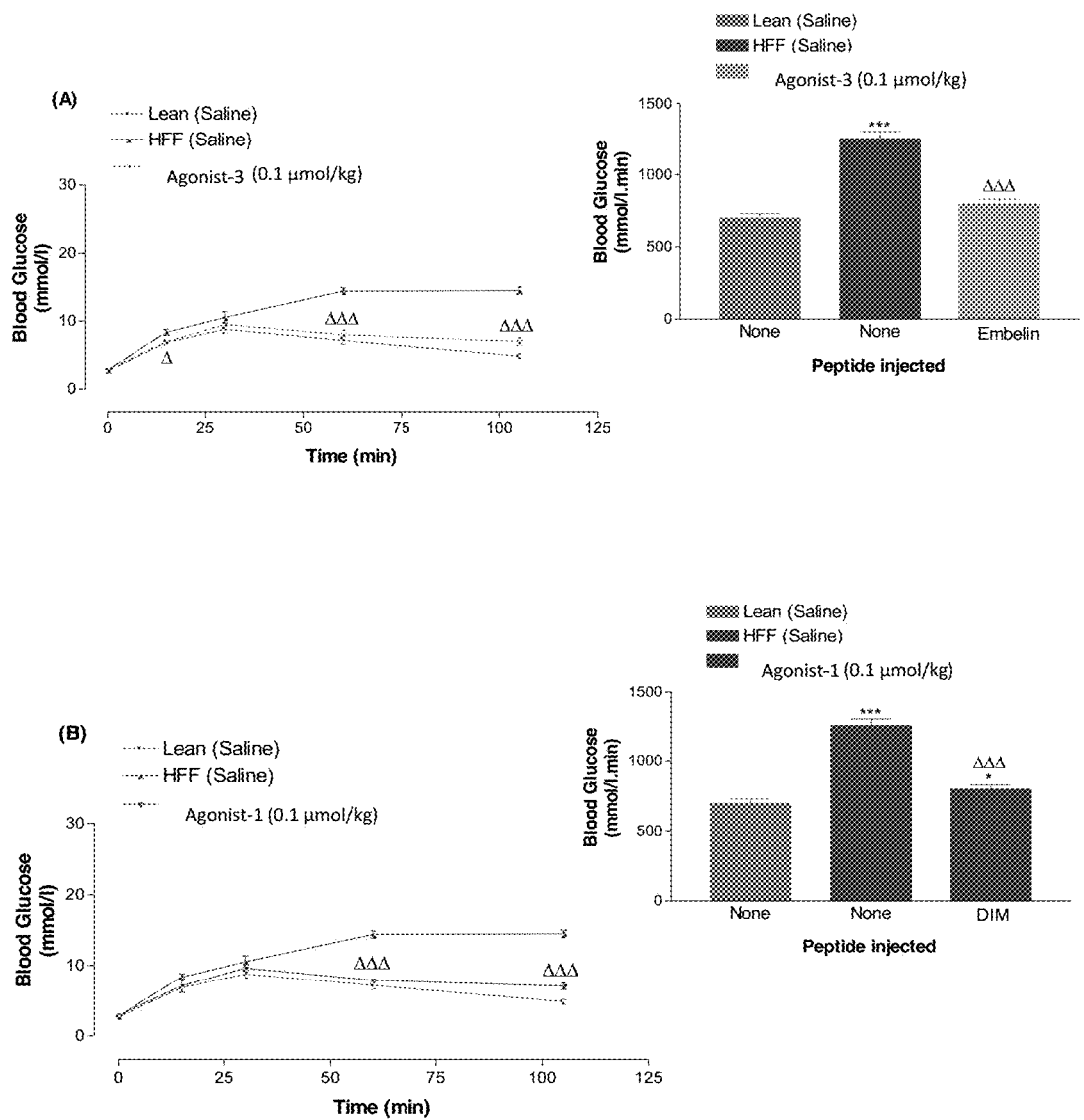

Blood glucose was measured prior to and after oral administration of glucose (18 mmol/kg body weight) in mice fed on a high-fat diet treated with daily injections of saline (control) or peptides for 21 days. Values are Mean ± SEM for 6 mice. * $P < 0.05$ and *** $P < 0.001$ compared to lean control. $^\Delta$ $P < 0.05$ and $^{\Delta\Delta\Delta}$ $P < 0.001$ compared to high-fat fed control.

Figure 21: Effects of daily administration of (A) Agonist-3 and (B) Agonist-1 on plasma insulin following oral administration of glucose to mice fed on a high-fat diet

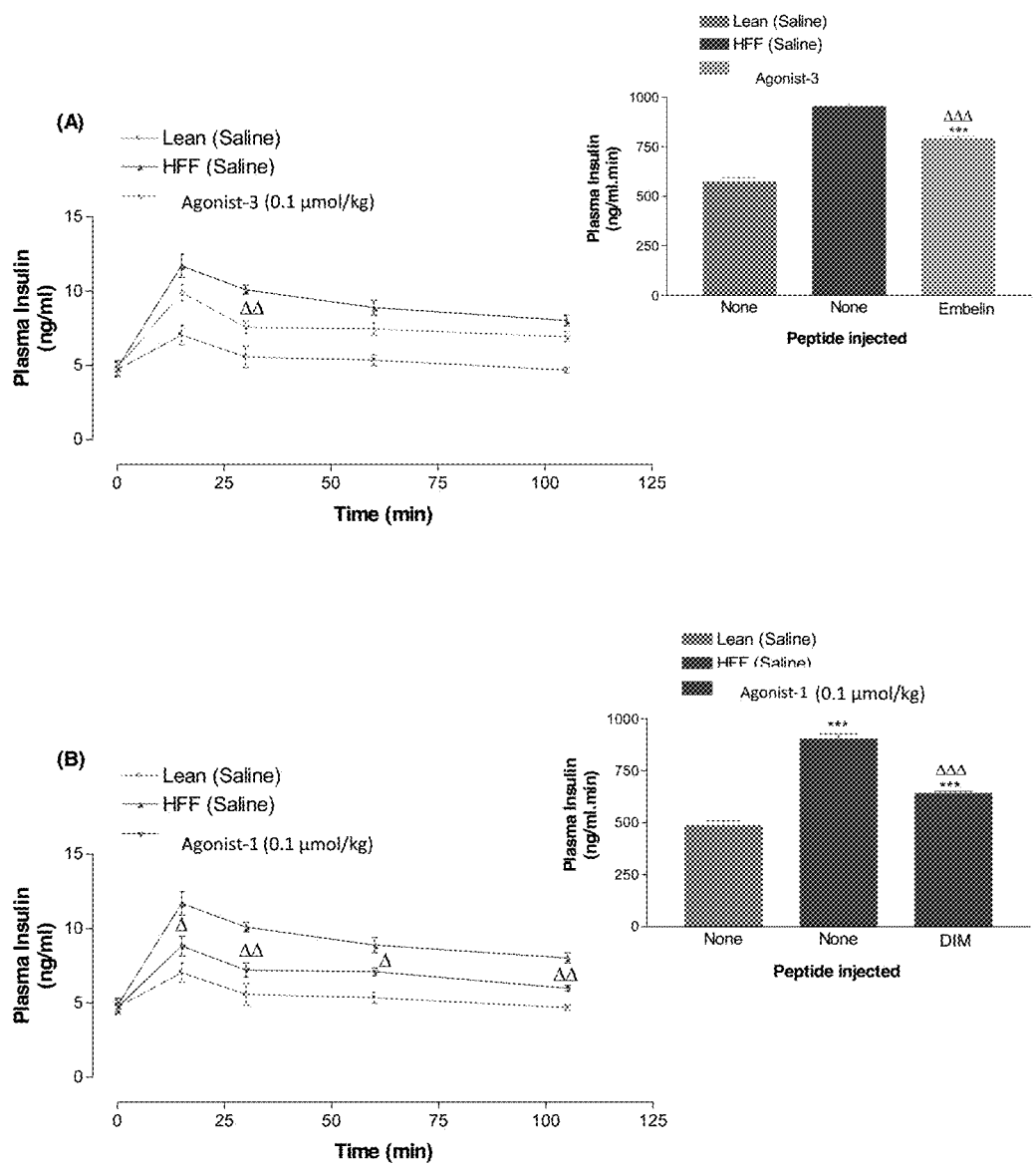

Plasma insulin was measured prior to and after oral administration of glucose (18 mmol/kg body weight) in mice fed on a high-fat diet treated with daily injections of saline (control) or peptides for 21 days. Values are Mean ± SEM for 6 mice. *** $P < 0.001$ compared to lean control. $^\Delta$ $P < 0.05$, $^{\Delta\Delta}$ $P < 0.01$ and $^{\Delta\Delta\Delta}$ $P < 0.001$ compared to high-fat fed control.

Figure 22: Effects of daily administration of Agonist-1 and Agonist-2 on pancreatic weight (A) and pancreatic insulin content (B) in mice fed on a high-fat diet

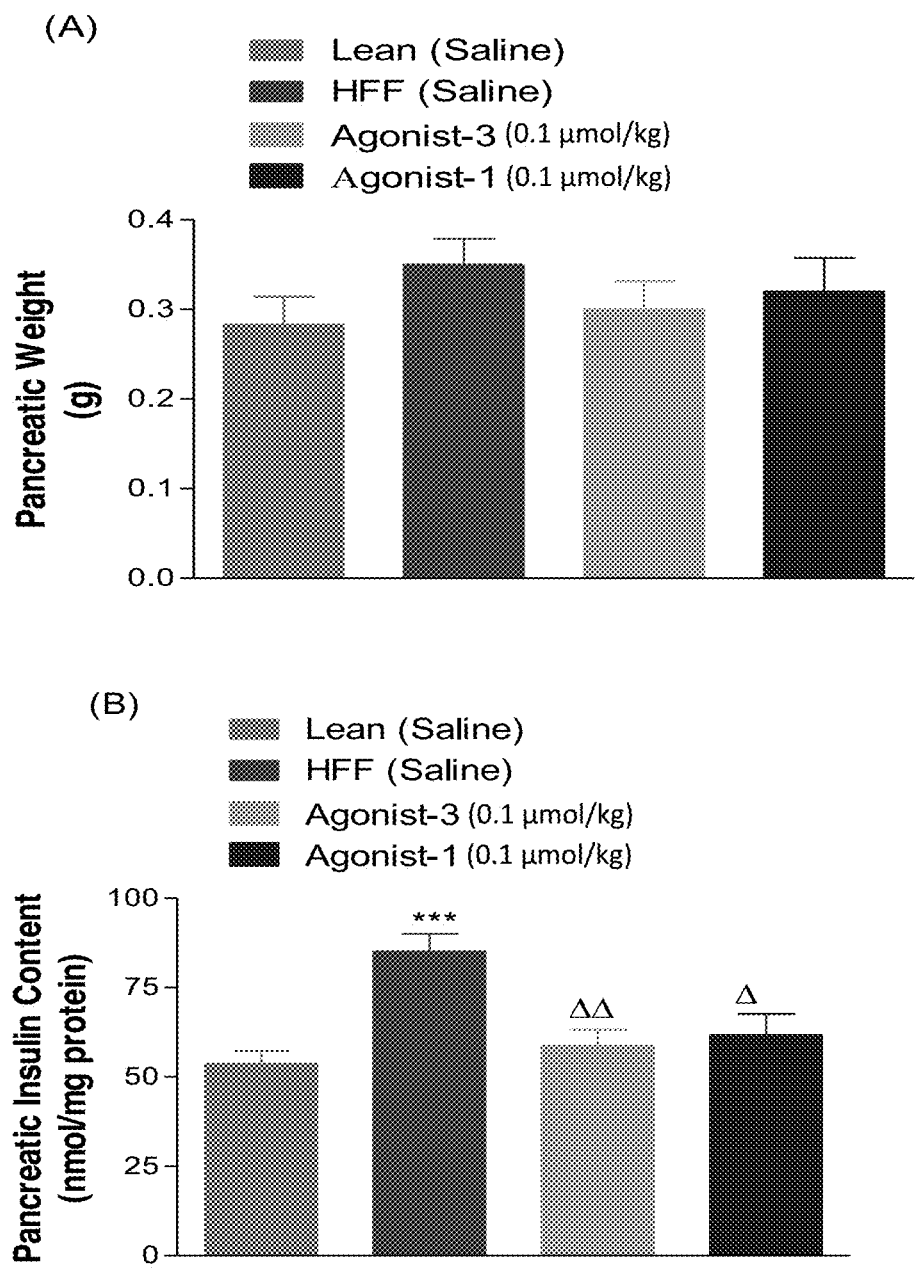

Mice were treated daily with saline (controls) or peptide (0.1 µmol/kg) for 21 days prior to excision of pancreas. Values ae expressed as Mean ± SEM for 6 mice. *** $P < 0.001$ compared to lean controls. $^{\Delta} P < 0.05$ and $^{\Delta\Delta} P < 0.01$ compared to high-fat fed controls.

Figure 23: Effects of daily administration of (A) Agonist-3 and (B) Agonist-1 on insulin sensitivity in mice fed on a high-fat diet

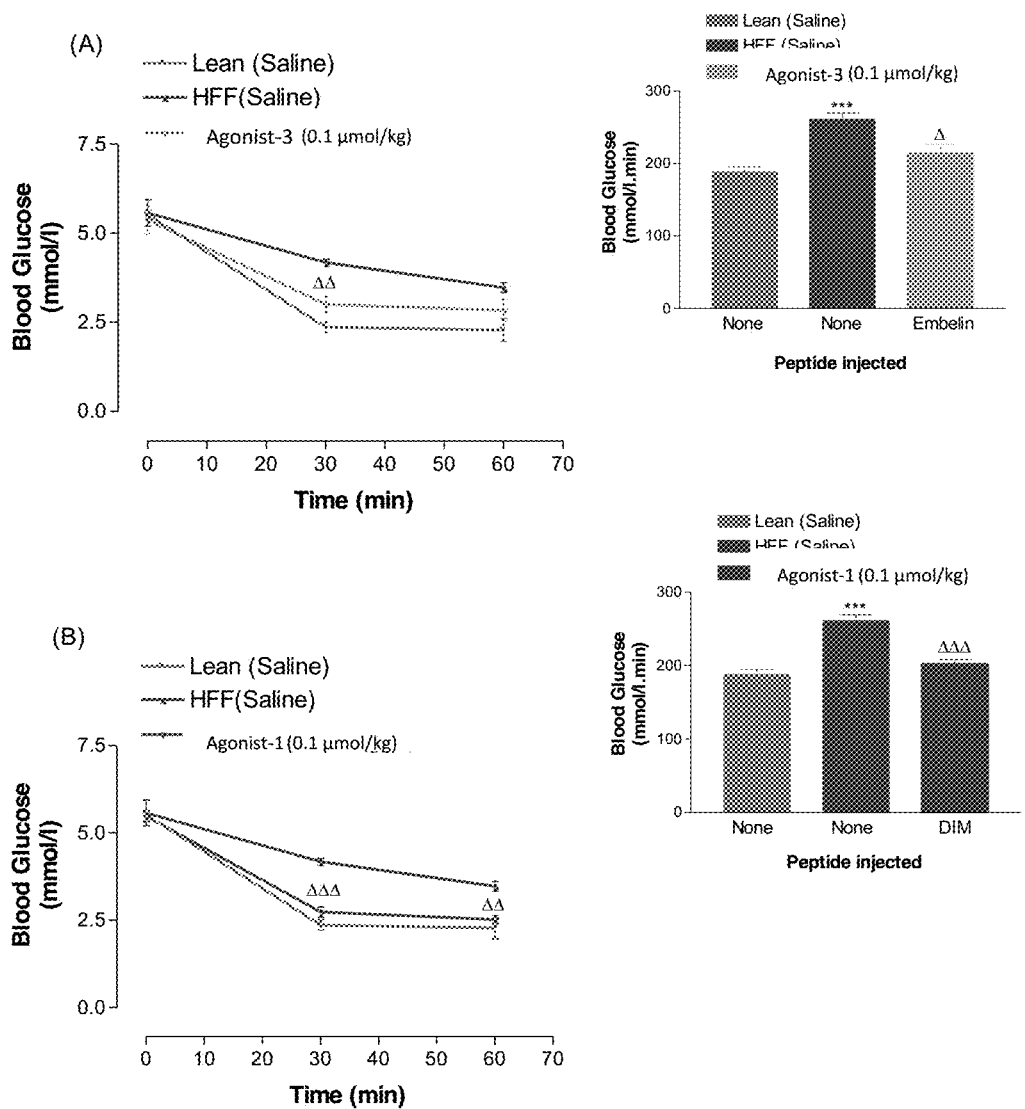

Blood glucose was measured prior to and after intraperitoneal administration of insulin (25 U/kg bw) in mice fed on a high-fat diet treated with daily oral administration of either saline (control) or ligand (0.1 µmol/kg) for 21 days. Values are Mean ± SEM for 6 mice. *** $P < 0.001$ compared to lean control. $^{\Delta\Delta}$ $P < 0.01$ and $^{\Delta\Delta\Delta}$ $P < 0.001$ compared to high-fat fed control.

Figure 24: Effects of daily administration of (A) Agonist-3 and (B) Agonist-1 on plasma GLP-1 concentration following oral administration of glucose to mice fed on a high-fat diet

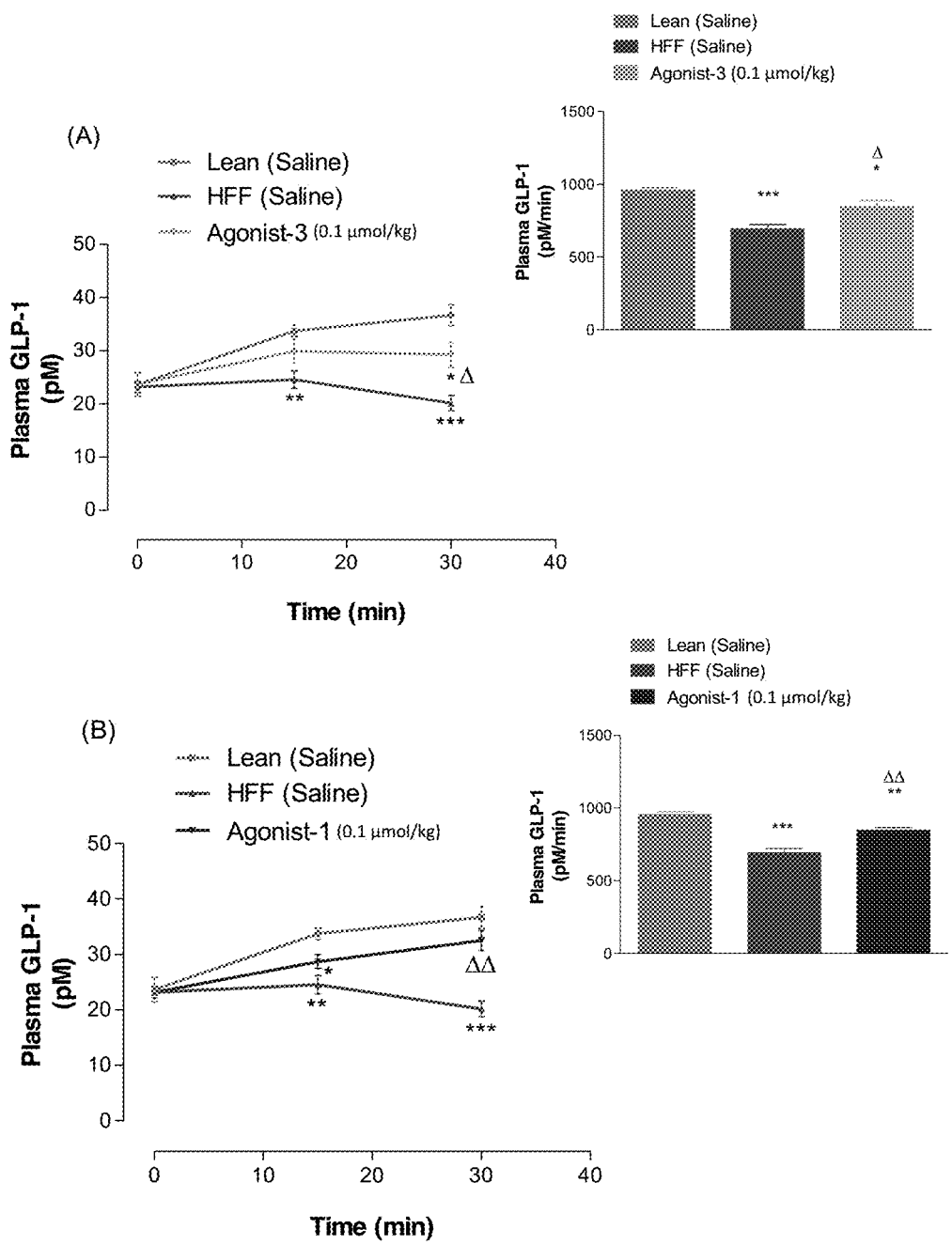

Plasma GLP-1 was measured prior to and after oral administration of glucose (18 mmol/kg body weight) in mice fed on a high-fat diet treated with daily injections of saline (control) or ligands for 21 days. Values are Mean ± SEM for 6 mice. * $P < 0.05$,  $P < 0.01$ and * $P < 0.001$ compared to lean control. $^\Delta$ $P < 0.05$ and $^{\Delta\Delta}$ $P < 0.01$ to high-fat fed control.

Figure 25: Plasma GLP-1 concentrations in lean mice and high-fat fed mice administered orally with saline (controls) or ligands for 21 days

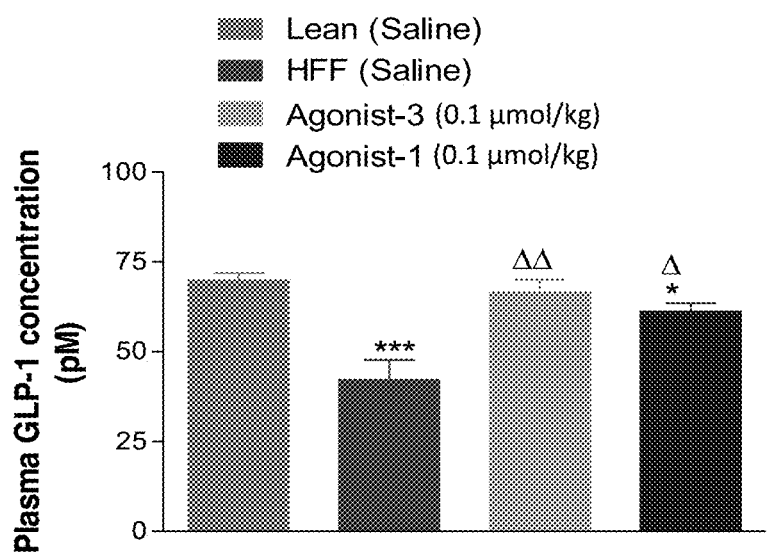

Mice were treated daily with saline (controls) or peptide (0.1 μmol/kg) for 21 days prior to measurement of GLP-1 concentration. Values ae expressed as Mean ± SEM for 6 mice. * $P < 0.05$ and *** $P < 0.001$ compared to lean controls. ᐃ $P < 0.05$ and ᐃᐃ $P < 0.01$ compared to high-fat fed controls.

Figure 26: Effects of daily administration of Agonist-1 and Agonist-3 on triglycerides (A), total cholesterol (B), HDL cholesterol (C) and LDL cholesterol (D) in mice fed on a high-fat diet
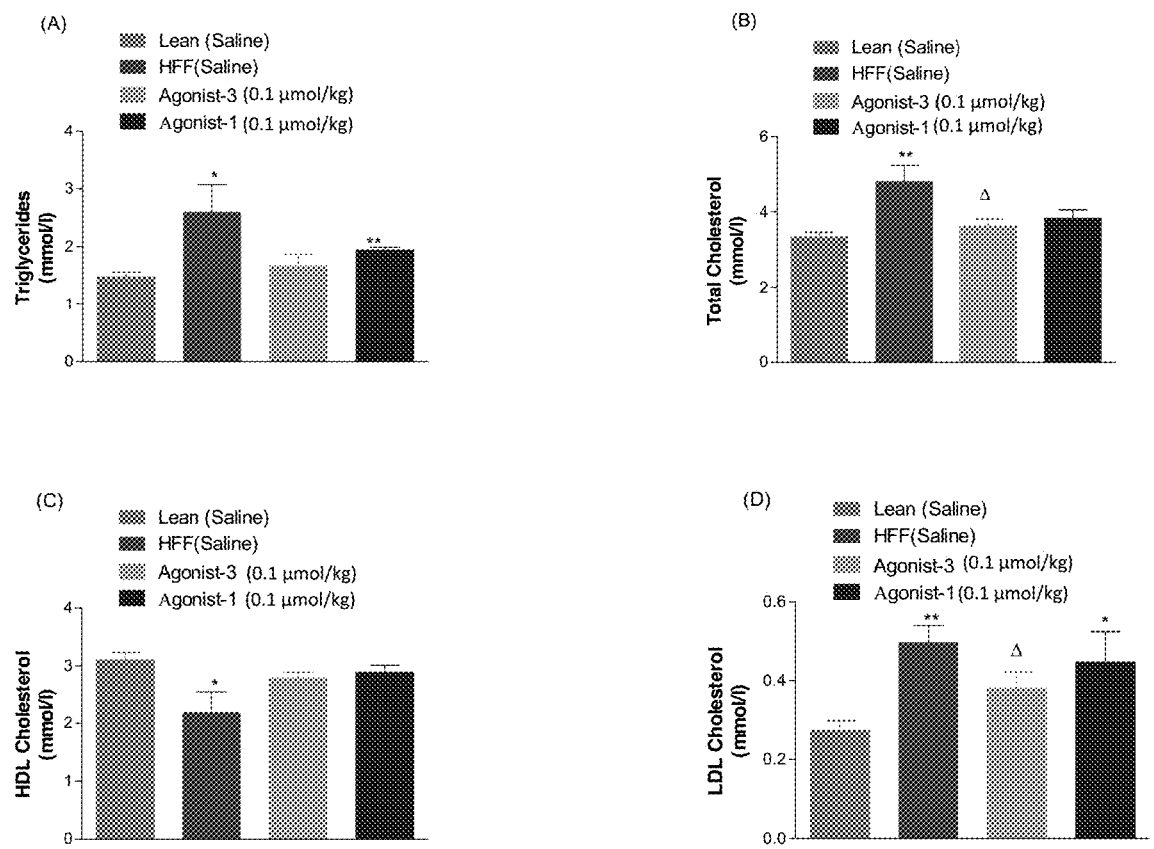
Values are Mean ± SEM for 6 mice. P < 0.05 and ** P < 0.01 compared to lean controls. Δ P < 0.05 compared to high-fat fed controls.

Figure 27: Effects of daily administration of Agonist-3 on lean body mass (A), body fat content (B and C) in mice fed on a high-fat diet
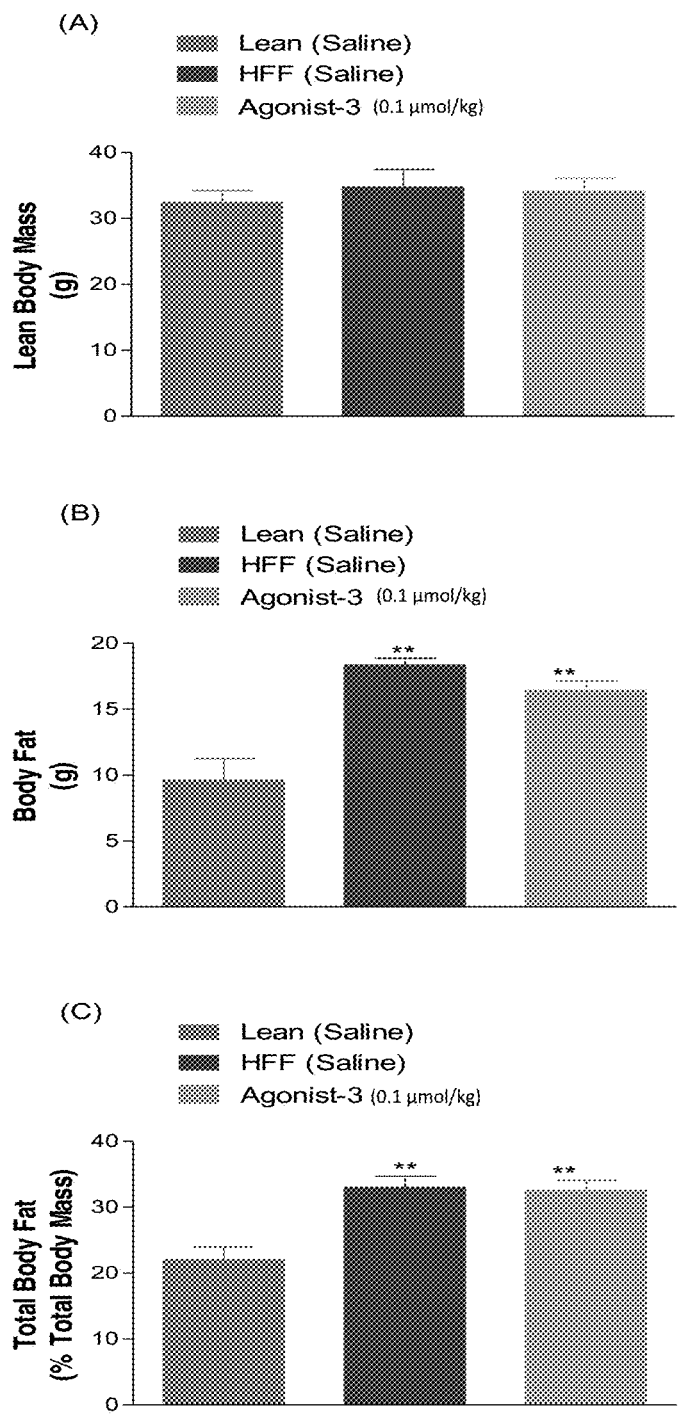
Values are Mean ± SEM for 6 mice. ** P < 0.01 compared to lean controls.

Figure 28: Effects of daily administration of Agonist-1 on lean body mass (A), body fat content (B and C) in mice fed on a high-fat diet
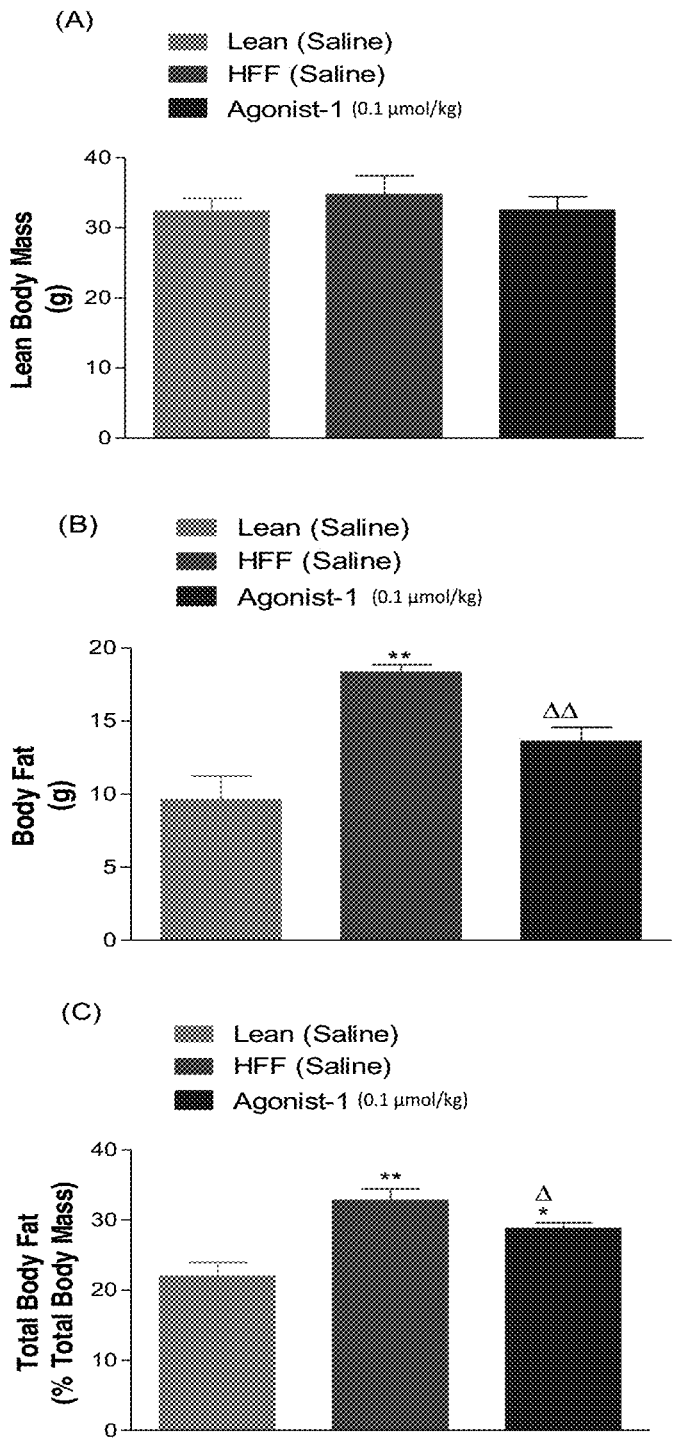
Values are Mean ± SEM for 6 mice. ** $P < 0.01$ compared to lean controls. $^{\Delta} P < 0.05$ and $^{\Delta\Delta} P < 0.01$ compared to high-fat fed controls.

Figure 29: Effects of daily administration of Agonist-3 on bone mineral density (A), bone mineral content (B) and bone area (C) in mice fed on a high-fat diet
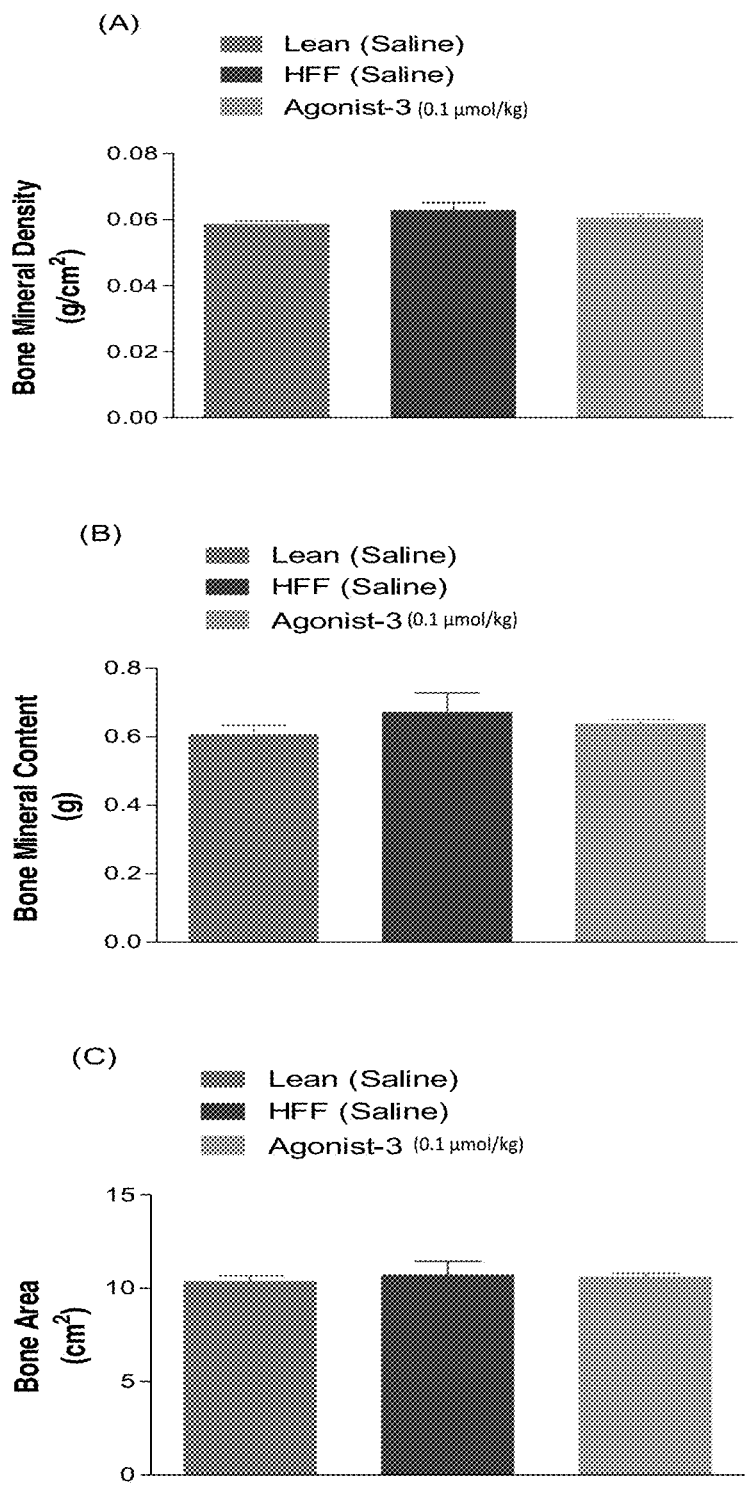
Values are Mean ± SEM for 6 mice.

Figure 30: Effects of daily administration of Agonist-1 on bone mineral density (A), bone mineral content (B) and bone area (C) in mice fed on a high-fat diet
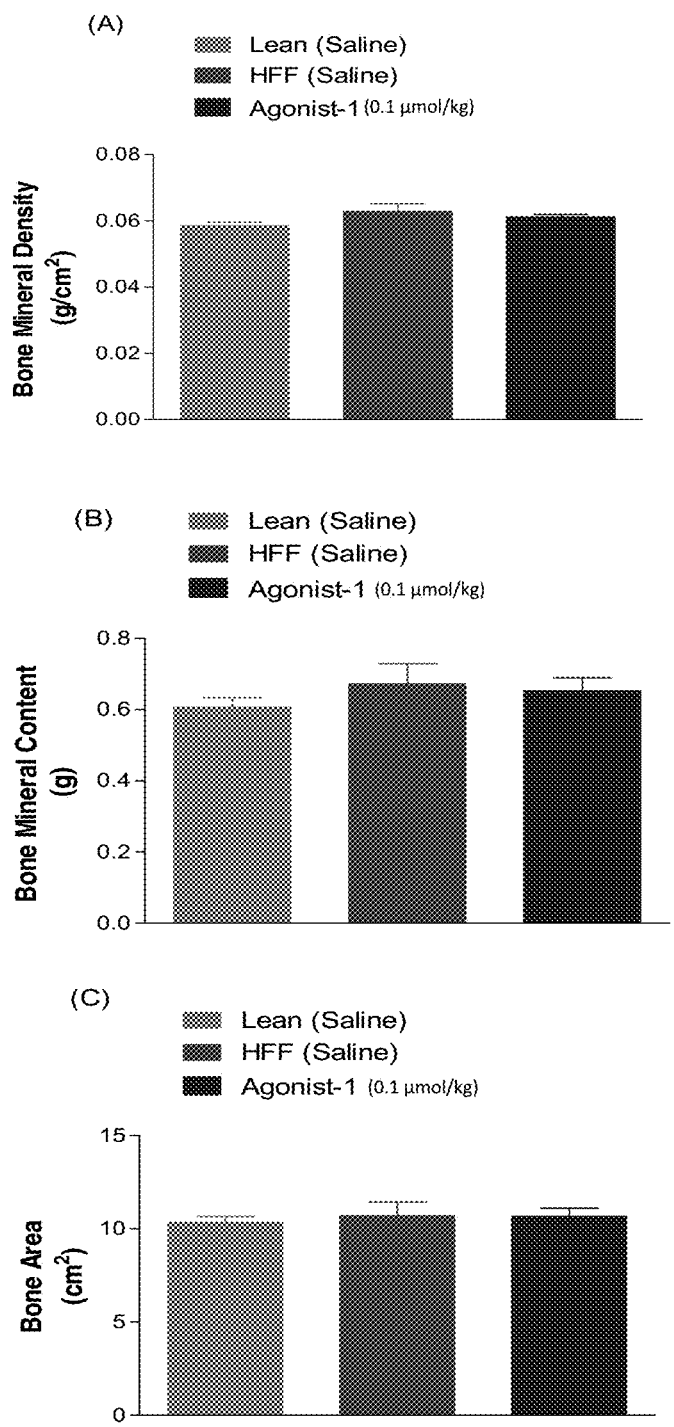
Values are Mean ± SEM for 6 mice.

COMPOSITIONS FOR USE IN THE TREATMENT OF DIABETES

This application is a continuation of U.S. application Ser. No. 15/749,351, filed Jan. 31, 2018, which is a national stage application under 35 U.S.C. § 371 of International Application No. PCT/EP2016/068183, filed Jul. 29, 2016, which claimed the benefit and priority of GB Application No. 1513543.7, filed Jul. 31, 2015. This application claims the benefit of and priority to each of the applications identified above, the contents of which are hereby incorporated by reference in their entireties.

FIELD OF THE INVENTION

This invention relates to compositions for use in the treatment of diabetes, for example type-2 diabetes; obesity; and/or metabolic syndrome.

BACKGROUND TO THE INVENTION

Diabetes is a major public health challenge with: at least 180 million reported cases of diabetes worldwide—a figure set to more than double by 2030 according to the World Health Organisation (WHO), consumption of 10% of Western healthcare budgets, and around 3.2 million deaths per year resulting from related complications. This alarming increase in incidence, coupled with the failure of established anti-diabetic drugs to tightly manage or control diabetes, demonstrates the market need for new innovation.

The worldwide increase in the incidence of obesity, metabolic syndrome, and type-2 diabetes demands the development of new drugs for safe and effective treatment, limiting the progression to long-term diabetic complications.

G-protein coupled receptor 84, also known as GPR84, (herein, GPR-a1), or inflammation-related G-protein coupled receptor EX33; is a receptor that has been identified on a number of tissues and is activated by medium chain fatty acids. GPR84 is a chemokine receptor that has been identified on peripheral blood leucocytes (neutrophils, T-lymphocytes, B-lymphocytes), spleen, adipocytes, bone marrow and lungs. GPR84 gene knockout in mice has found that the receptor has a role in interleukin-4 (IL-4) gene expression, highlighting the potential of GPR84 as a new therapeutic target, and opening new avenues, such as identification of new specific agonists for GPR84 as new effective treatments for diabetes.

SUMMARY OF THE INVENTION

According to a first aspect of the present invention, there is provided a composition for use in the treatment of diabetes, the composition comprising at least one of diindolylmethane; indole-3-carbinol; embelin; [6]-gingerol; and [6]-shogaol, or combinations each thereof.

According to a second aspect of the present invention, there is provided use of at least one of diindolylmethane; indole-3-carbinol; embelin; [6]-gingerol; and [6]-shogaol, or combinations each thereof in the manufacture of a medicament composition for the treatment of diabetes.

According to a third aspect of the present invention, there is provided a method for the treatment of diabetes, the method comprising the steps of administering a composition comprising at least one of diindolylmethane; indole-3-carbinol; embelin; [6]-gingerol; and [6]-shogaol, or combinations each thereof.

Also disclosed is a composition for use in altering, optionally increasing, insulin release, the composition comprising at least one of diindolylmethane; indole-3-carbinol; embelin; [6]-gingerol; and [6]-shogaol, or combinations each thereof.

Also disclosed is use of at least one of diindolylmethane; indole-3-carbinol; embelin; [6]-gingerol; and [6]-shogaol, or combinations each thereof in the manufacture of a medicament composition for altering, optionally increasing, insulin release.

Also disclosed is a method for altering, optionally increasing, insulin release, the method comprising the steps of administering a composition comprising at least one of diindolylmethane; indole-3-carbinol; embelin; [6]-gingerol; and [6]-shogaol, or combinations each thereof.

Optionally, the method comprises the step of administering a pharmaceutically acceptable amount of the composition comprising at least one of diindolylmethane; indole-3-carbinol; embelin; [6]-gingerol; and [6]-shogaol, or combinations each thereof.

Further optionally, the method comprises the step of administering a pharmaceutically acceptable amount of the composition comprising at least one of diindolylmethane; indole-3-carbinol; embelin; [6]-gingerol; and [6]-shogaol, or combinations each thereof to a subject in need thereof.

Further optionally, the method comprises the step of administering a pharmaceutically acceptable amount of the composition comprising at least one of diindolylmethane; indole-3-carbinol; embelin; [6]-gingerol; and [6]-shogaol, or combinations each thereof to a subject suffering from diabetes.

Optionally, the composition comprises a pharmaceutically acceptable amount at least one of diindolylmethane; indole-3-carbinol; embelin; [6]-gingerol; and [6]-shogaol, or combinations each thereof.

Further optionally, the composition comprises from $10^{-12}$ to $10^{-4}$ mol/L of at least one of diindolylmethane; indole-3-carbinol; embelin; [6]-gingerol; and [6]-shogaol, or of a combination each thereof.

Still further optionally, the composition comprises $10^{-4}$ mol/L of at least one of diindolylmethane; indole-3-carbinol; embelin; [6]-gingerol; and [6]-shogaol, or of a combination each thereof.

Optionally, the composition further comprises glucose.

Further optionally, the composition further comprises 5.6 mM glucose.

Alternatively, the composition further comprises 16.7 mM glucose.

Optionally, the glucose is administered before the at least one of diindolylmethane; indole-3-carbinol; embelin; [6]-gingerol; and [6]-shogaol, or the combination each thereof.

Optionally or additionally, the glucose is co-administered with the at least one of diindolylmethane; indole-3-carbinol; embelin; [6]-gingerol; and [6]-shogaol, or the combination each thereof.

Optionally or additionally, the glucose is administered after the at least one of diindolylmethane; indole-3-carbinol; embelin; [6]-gingerol; and [6]-shogaol, or the combination each thereof.

Optionally, the composition comprises diindolylmethane (3,3'-methanediylbis(1H-indole)).

Further optionally, the composition comprises a pharmaceutically acceptable amount of diindolylmethane (3,3'-methanediylbis(1H-indole)).

Still further optionally, the composition comprises from $10^{-9}$ to $10^{-4}$ mol/L of diindolylmethane (3,3'-methanediylbis (1H-indole)).

Still further optionally, the composition comprises from $10^{-8}$ to $10^{-4}$ mol/L of diindolylmethane (3,3'-methanediylbis (1H-indole)) and 5.6 mM glucose.

Further alternatively, the composition comprises from $10^{-9}$ to $10^{-4}$ mol/L of diindolylmethane (3,3'-methanediylbis (1H-indole)) and 16.7 mM glucose.

Optionally or additionally, the composition comprises indole-3-carbinol (1H-Indol)-3-ylmethanol).

Further optionally, the composition comprises a pharmaceutically acceptable amount of indole-3-carbinol (1H-Indol-3-ylmethanol).

Still further optionally, the composition comprises $10^{-7}$-$10^{-4}$ mol/L of indole-3-carbinol (1H-Indol-3-ylmethanol) and 5.6 mM glucose.

Still further optionally, the composition comprises $10^{-6}$-$10^{-4}$ mol/L of indole-3-carbinol (1H-Indol-3-ylmethanol) and 16.7 mM glucose.

Optionally or additionally, the composition comprises embelin (2,5-dihydroxy-3-undecylcyclohexa-2,5-diene-1,4-dione).

Further optionally, the composition comprises a pharmaceutically acceptable amount of embelin (2,5-dihydroxy-3-undecylcyclohexa-2,5-diene-1,4-dione).

Still further optionally, the composition comprises from $10^{-10}$ to $10^{-4}$ mol/L of embelin (2,5-dihydroxy-3-undecylcyclohexa-2,5-diene-1,4-dione).

Still further optionally, the composition comprises from $10^{-9}$ to $10^{-4}$ mol/L of embelin (2,5-dihydroxy-3-undecylcyclohexa-2,5-diene-1,4-dione) and 5.6 mM glucose.

Alternatively, the composition comprises from $10^{-10}$ to $10^{-4}$ mol/L of embelin (2,5-dihydroxy-3-undecylcyclohexa-2,5-diene-1,4-dione) and 16.7 mM glucose.

Optionally or additionally, the composition comprises [6]-gingerol ((5S)-5-hydroxy-1-(4-hydroxy-3-methoxyphenyl)decan-3-one).

Further optionally, the composition comprises a pharmaceutically acceptable amount of [6]-gingerol ((5S)-5-hydroxy-1-(4-hydroxy-3-methoxyphenyl)decan-3-one).

Still further optionally, the composition comprises from $10^{-8}$ to $10^{-4}$ mol/L of [6]-gingerol ((5S)-5-hydroxy-1-(4-hydroxy-3-methoxyphenyl)decan-3-one).

Still further optionally, the composition comprises from $10^{-8}$ to $10^{-4}$ mol/L of [6]-gingerol ((5S)-5-hydroxy-1-(4-hydroxy-3- methoxyphenyl)decan-3-one) and 5.6 mM glucose.

Alternatively, the composition comprises from $10^{-8}$ to $10^{-4}$ mol/L of [6]-gingerol ((5S)-5-hydroxy-1-(4-hydroxy-3- methoxyphenyl)decan-3-one) and 16.7 mM glucose.

Optionally or additionally, the composition comprises [6]-shogaol ((E)-1-(4-hydroxy-3-methoxyphenyl)dec-4-en-3-one).

Further optionally, the composition comprises a pharmaceutically acceptable amount of [6]-shogaol ((E)-1-(4-hydroxy-3-methoxyphenyl)dec-4-en-3-one).

Still further optionally, the composition comprises a pharmaceutically acceptable amount of [6]-shogaol ((E)-1-(4-hydroxy-3-methoxyphenyl)dec-4-en-3-one) and 5.6 mM glucose.

Still further optionally, the composition comprises a pharmaceutically acceptable amount of [6]-shogaol ((E)-1-(4-hydroxy-3-methoxyphenyl)dec-4-en-3-one) and 16.7 mM glucose.

Optionally, the composition is administered in an amount such that the at least one of diindolylmethane; indole-3-carbinol; embelin; [6]-gingerol; and [6]-shogaol, or combinations each thereof is administered in an amount of 0.1 μmol/kg to 50 μmol/kg body weight.

Further optionally, the composition is administered in combination with glucose in an amount such that the glucose is administered in an amount of 18 mmol/kg body weight.

According to a further aspect of the present invention, there is provided a composition for use in the treatment of obesity, the composition comprising at least one of diindolylmethane; indole-3-carbinol; embelin; [6]-gingerol; and [6]-shogaol, or combinations each thereof.

According to a still further aspect of the present invention, there is provided use of at least one of diindolylmethane; indole-3-carbinol; embelin; [6]-gingerol; and [6]-shogaol, or combinations each thereof in the manufacture of a medicament composition for the treatment of obesity.

According to a still further aspect of the present invention, there is provided a method for the treatment of obesity, the method comprising the steps of administering a composition comprising at least one of diindolylmethane; indole-3-carbinol; embelin; [6]-gingerol; and [6]-shogaol, or combinations each thereof.

According to a further aspect of the present invention, there is provided a composition for use in the treatment of metabolic syndrome, the composition comprising at least one of diindolylmethane; indole-3-carbinol; embelin; [6]-gingerol; and [6]-shogaol, or combinations each thereof.

According to a still further aspect of the present invention, there is provided use of at least one of diindolylmethane; indole-3-carbinol; embelin; [6]-gingerol; and [6]-shogaol, or combinations each thereof in the manufacture of a medicament composition for the treatment of metabolic syndrome.

According to a still further aspect of the present invention, there is provided a method for the treatment of metabolic syndrome, the method comprising the steps of administering a composition comprising at least one of diindolylmethane; indole-3-carbinol; embelin; [6]-gingerol; and [6]-shogaol, or combinations each thereof.

According to a still further aspect of the present invention, there is provided a composition for use in the treatment of any one of diabetes, obesity, or metabolic syndrome; the composition comprising at least one of capric acid (decanoic acid), undecanoic acid, lauric acid (dodecanoic acid), and tridecanoic acid; or combinations each thereof.

BRIEF DESCRIPTION OF THE DRAWINGS

Embodiments of the present invention will now be demonstrated by way of non-limiting examples and in reference to the accompanying drawings in which:

FIG. 1 illustrates double immunofluorescence of GPR84 co-localised with insulin in clonal pancreatic BRIN-BD11 cells;

FIG. 2 illustrates cellular localisation of GPR84 with insulin and glucagon in mouse pancreatic tissue;

FIG. 3 illustrates the effect of diindolylmethane on insulin secretion and LDH release from clonal BRIN-BD11 cells at 5.6 mM glucose;

FIG. 4 illustrates the effect of diindolylmethane on insulin secretion and LDH release from clonal BRIN-BD11 cells at 16.7 mM glucose;

FIG. 5 illustrates the effect of embelin on insulin secretion and LDH release from clonal BRIN-BD11 cells at 5.6 mM glucose;

FIG. 6 illustrates the effect of embelin on insulin secretion and LDH release from clonal BRIN-BD11 cells at 16.7 mM glucose;

FIG. 7 illustrates the effect of compositions of the present invention and alanine on intracellular Ca2+ from clonal BRIN-BD11 cells at 5.6 mM glucose;

FIG. 8 illustrates the effect of medium chain fatty acids and alanine on intracellular Ca2+ from clonal BRIN-BD11 cells at 5.6 mM glucose;

FIG. 9 illustrates the effect of medium chain fatty acids and alanine on intracellular Ca2+ from clonal BRIN-BD11 cells at 16.7 mM glucose;

FIG. 10 illustrates the effect of compositions of the present invention and alanine on intracellular Ca2+ from clonal BRIN-BD11 cells at 16.7 mM glucose;

FIG. 11 illustrates the effect of compositions of the present invention and glucagon-like peptide-1 (GLP-1) on cAMP production from clonal BRIN-BD11 cells at 11.1 mM glucose;

FIG. 12 illustrates acute effects of compositions of the present invention on plasma glucose in NIH Swiss mice on normal chow and high fat diet following glucose load;

FIG. 13 illustrates acute effects of medium chain fatty acids on plasma glucose in NIH Swiss mice on normal chow and high fat diet following glucose load;

FIG. 14 illustrates acute effects of compositions of the present invention on plasma glucose and plasma insulin in NIH Swiss mice on normal chow and high fat diet following glucose load;

FIG. 15 illustrates the effects of daily administration of (A) Embelin and (B) Diindolylmethane on non-fasting blood glucose in mice fed on a high-fat diet;

FIG. 16 illustrates the effects of daily administration of (A) Embelin and (B) Diindolylmethane on non-fasting plasma insulin in mice fed on a high-fat diet;

FIG. 17 illustrates the effects of daily administration of (A) Embelin and (B) Diindolylmethane on body weight in mice fed on a high-fat diet;

FIG. 18 illustrates the effects of daily administration of (A) Embelin and (B) Diindolylmethane on energy intake in mice fed on a high-fat diet;

FIG. 19 illustrates the effects of daily administration of (A) Embelin and (B) Diindolylmethane on fluid intake in mice fed on a high-fat diet;

FIG. 20 illustrates the effects of daily administration of (A) Embelin and (B) Diindolylmethane on blood glucose following oral administration of glucose to mice fed on a high-fat diet;

FIG. 21 illustrates the effects of daily administration of (A) Embelin and (B) Diindolylmethane on plasma insulin following oral administration of glucose to mice fed on a high-fat diet;

FIG. 22 illustrates the effects of daily administration of Diindolylmethane and Indole-3-carbinol on pancreatic weight (A) and pancreatic insulin content (B) in mice fed on a high-fat diet;

FIG. 23 illustrates the effects of daily administration of (A) Embelin and (B) Diindolylmethane on insulin sensitivity in mice fed on a high-fat diet;

FIG. 24 illustrates the effects of daily administration of (A) Embelin and (B) Diindolylmethane on plasma GLP-1 concentration following oral administration of glucose to mice fed on a high-fat diet;

FIG. 25 illustrates plasma GLP-1 concentrations in lean mice and high-fat fed mice administered orally with saline (controls) or compositions of the present invention for 21 days;

FIG. 26 illustrates the effects of daily administration of Diindolylmethane and Embelin on triglycerides total cholesterol (B), HDL cholesterol (C) and LDL cholesterol (D) in mice fed on a high-fat diet;

FIG. 27 illustrates the effects of daily administration of Embelin on lean body mass (A), body fat content (B and C) in mice fed on a high-fat diet;

FIG. 28 illustrates the effects of daily administration of Diindolylmethane on lean body mass (A), body fat content (B and C) in mice fed on a high-fat diet;

FIG. 29 illustrates the effects of daily administration of Embelin on bone mineral density (A), bone mineral content (B) and bone area (C) in mice fed on a high-fat diet; and FIG. 30 illustrates the effects of daily administration of Diindolylmethane on bone mineral density (A), bone mineral content (B) and bone area (C) in mice fed on a high-fat diet.

For the avoidance of doubt, the following terms are used synonymously herein:
GPR-a1 GPR84, inflammation-related G-protein coupled receptor EX33
MCFA1 Alanine
MCFA2 Tridecanoic acid
MCFA3 Lauric acid (dodecanoic acid)
MCFA4 Undecanoic acid
MCFA5 Capric acid (decanoic acid)
Agonist-1 DIM, Diindolylmethane
Agonist-2 Indole-3-carbinol
Agonist-3 Embelin
Agonist-4 [6]-Gingerol
Agonist-5 [6]-Shogaol Materials and Methods Insulin Secretion Insulin-secreting BRIN-BD11 cells were cultured with RPMI-1640 media (11.1 mM glucose) containing antibiotics (100 U/ml penicillin and 0.1 mg/ml streptomycin) and 10% foetal calf serum at 37° C. in an atmosphere of 95% air and 5% carbon dioxide. For acute insulin secretion studies, cells were detached using trypsin/EDTA and incubated overnight in 24 well plates with 150,000 cells per well. Cells were then pre-incubated for 40 minutes at 1.1 mmol/l glucose in Krebs buffer (comprising 4.7 mmol/l KCL, 115 mmol/l NaCl, 1.28 mmol/CaCl2, 10 mmol/l NaHCO3, 5 g/l BSA, 1.2 mmol/l KH2PO4, 1.2 mmol/l MgSO47H2O pH 7.4). Test incubations were then performed at 37° C. for 20 minutes. DIM, indole-3-carbinol, embelin, [6]-gingerol, and [6]-shogaol at $10^{-12}$-$10^{-4}$ mol/L were tested at both 5.6 mmol/L and 16.7 mmol/L glucose, as indicated in the accompanying drawings. Supernatants were removed, evaluated for lactate dehydrogenase (LDH) release as an indicator of cytotoxicity (as per manufacturer's protocol) or frozen at −20° C. until determination of insulin by radioimmunoassay.

Pancreatic islets were isolated from normal mice derived from the colony maintained at the University of Ulster, UK by collagenase digestion. After overnight culture as above, groups of 10 islets were incubated for 1 hour at 37° C. in 1 ml of 1.1 mmol/l glucose Krebs. Test incubations were then carried out for 1 hour at 11.1 mmol/l glucose with various GPR120 agonists ($10^{-10}$-$10^{-4}$ mol/L). Insulin release and insulin content of islets, treated overnight with 1 ml acid ethanol, were determined by radioimmunoassay.

Intracellular Ca2+ and cAMP

For intracellular Ca2+ measurement, monolayers of BRIN-BD11 cells were seeded overnight at a density of 80,000 cells per well in a 96-well black walled clear bottom plate. Cells were washed with 100 μl of Krebs buffer and incubated for 1 hour with Flex calcium assay kit reagent at 37° C. GPR84 at $10^{-4}$ mol/L were added at 5.6 mmol/L and 16.7 mmol/L glucose. Fluorometric data were obtained using the FLEX Station scanner and test solutions were transferred using fluid transfer workstation at a wavelength of 525 nm (Molecular Devices). For cAMP determination, BRIN-BD11 cells were seeded in a 96-well plate at a density of 30,000 cells per well. Cells were washed with 300 µl Krebs buffer for 40 min and 150 µl of compositions of the present invention at $10^{-10}$-$10^{-4}$ mol/L were tested at 11.1 mol/L glucose. After 20 minutes, test solutions were removed and 0.1M HCL (150 µL) was added to lyse the cells. Total cAMP production in the cell supernatants were measured using cAMP enzyme immunoassay kit according to the manufacturer's protocol (Sigma, Poole, UK).

Histology

BRIN-BD11 cells were allowed to attach overnight to polylysine-coated slides and fixed using 4% paraformaldehyde/PBS. Antigen retrieval was achieved by incubation in sodium citrate (50 mmol/l) at 90° C. for 20 minutes. Pancreatic tissues from normal mice were fixed in 4% PFA/PBS, embedded in paraffin wax and sections cut at 8 µm. Sections were mounted onto polylysine-coated slides and dried on a hot plate. Pancreatic sections were de-waxed and antigen retrieval performed as described above. Slides were incubated overnight at 4° C. with guinea pig anti-insulin (1:500), guinea pig anti-glucagon (1:500) and rabbit anti-GPR84 antibodies (1:100). After washing in PBS, sections were incubated with Alexa Fluor 488 fluorescein goat anti-rabbit or anti-guinea pig IgG and anti-guinea pig or anti-rabbit Alexa 594 nm IgG (1:400; Molecular Probes (Life Technologies Ltd, Paisley, UK)) for 45 minutes at 37° C. and DAPI nuclear stain for 15 minutes at 37° C. Finally slides were washed in PBS, mounted and analysed using a BX51 Olympus microscope equipped with an Olympus XM10 digital camera. Relative GPR84 quantification analysis was performed on BRIN-BD11 cells after exposure to compositions of the present invention at $10^{-4}$ mol/L at 11.1 mmol/L glucose for 20 minutes. GPR84 and insulin immunofluorescence staining was performed as described above. Analysis was performed by Cell-F software (closed polygon icon), with >200 cells per treatment group. All slides were blinded and a negative control slide was performed to ensure antibody specificity with omission of the primary antibody.

Statistics

Data are expressed as the mean±the standard error of the mean (SEM). Results were compared using the Student's t-test or one-way ANOVA on Prism graph pad version 5.0. Differences in data were considered to be statistically significant for $p<0.05$.

Animals

Adult male (20-22 week) NIH Swiss mice (Harlan UK Ltd) were individually housed in an air-conditioned room at 22±2° C. with 12 hour light: 12 hour darkness cycles. Drinking water and standard rodent maintenance diet (Trouw Nutrition, Cheshire, UK) were supplied ad libitum. Non-fasted NIH Swiss mice (n=6) received an oral injection of glucose alone (18 mmol/kg body weight) or in combination with compositions of the present invention (50 µmol/kg body weight). Blood samples were obtained from the cut tip from tail vein of conscious mice and centrifuged at 13,000 rpm for 3 minutes at 4° C. Plasma glucose was measured by an automated glucose oxidase procedure using a Beckman glucose analyser and insulin determined by radioimmunoassay. All animal experiments were carried out in accordance with the UK Animal (Scientific Procedures) Act 1986.

Administration in High Fat Fed Diabetic Mice

Daily oral administration of compositions of the present invention (0.1 µmol/kg body weight) or saline vehicle (0.9% w/v NaCl) were utilised in a long term study (28 days) examining their effects on high fat fed diabetic NIH Swiss mice. In order to confirm diabetes, an oral glucose tolerance test (OGTT) was performed. Food intake, fluid intake, body weight, non-fasted plasma glucose and insulin concentrations were monitored every 2- to 4-days as indicated in the accompanying drawings. At the end of the study, glucose tolerance (18 mmol/kg body weight) and insulin sensitivity (25 U/kg body weight) were assessed. Mice were anesthetised by isoflurane and killed by cervical dislocation. Dual energy X-ray absorption (DEXA) scanning was performed after prior calibration and quality control with the aluminium/lucite phantom (0.069 g/cm2, 12.0% fat) using a PIXImus system (software version 1.4x).

EXAMPLES

Example 1—Expression of GPR84 in BRIN-BD11 Cells and Mouse Islets

Distribution of insulin and GPR84 were investigated in BRIN-BD11 cells. DAPI (blue) stained nuclei (FIG. 1A), and insulin (green) were distributed across the BRIN-BD11 cells (FIG. 1B) with a similar staining pattern to GPR84 (red) (FIG. 1C). Double immunofluorescence combination of insulin with GPR84 indicated areas of co-localisation (yellow) (FIG. 1D), demonstrating the presence of GPR-a1 in pancreatic beta cells. The distribution of DAPI, insulin, glucagon and GPR84 in mouse pancreatic islets are shown in FIG. 2. DAPI (blue) displayed the nuclei in pancreatic islets (FIG. 2A,B), GPR84 (green) was expressed throughout the islet with a similar staining pattern to insulin (red) (FIG. 2C,D). Merge of insulin and GPR84 indicated that insulin secreting beta cells express GPR84 (FIG. 2G) while there was no evidence of the GPR84 receptor in glucagon secreting alpha cells (FIG. 2H). While no co-localisation was displayed on glucagon secreting alpha cells, the effect of GPR84 on beta cells may result in paracrine effects on other pancreatic islet cells.

Example 2—Effects of Compositions of the Present Invention on Insulin Secretion from BRIN-BD11 Cells Insulin releasing properties of compositions of the present invention at $10^{-12}$-$10^{-4}$ mol/L were assessed in clonal BRIN-BD11 cells at 5.6 mM and 16.7 mM glucose. Diindolylmethane at $10^{-8}$-$10^{-4}$ mol/L enhanced insulin release (EC50 $1.3 \times 10^{-7}$ mol/L) ($p<0.05$-$p<0.001$) (FIG. 3A) at 5.6 mM basal glucose concentrations. At stimulatory glucose concentrations (16.7 mM glucose), Diindolylmethane significantly enhanced insulin release at $10^{-9}$-$10^{-4}$ mol/L (EC50 $1.0 \times 10^{-6}$ mol/L) ($p<0.05$-$p<0.001$) (FIG. 4A). No cytotoxicity was found with Diindolylmethane at 5.6 mM glucose (FIG. 3B) and 16.7 mM glucose (FIG. 4B).

Embelin at $10^{-9}$-$10^{-4}$ mol/L enhanced insulin release ($p<0.05$-$p<0.001$) (EC50 of $7.3 \times 10^{-7}$ mol/L) (FIG. 5A) at 5.6 mM basal glucose concentrations. At stimulatory glucose concentrations (16.7 mM glucose), Embelin enhanced insulin release at $10^{-10}$-$10^{-4}$ mol/L ($p<0.01$-$p<0.001$) (EC50 of $2.1\times10^{-7}$ mol/L) (FIG. 6A). No cytotoxicity was found with Embelin at 5.6 mM glucose (FIG. 5B) and 16.7 mM glucose (FIG. 6B).

Indole-3-carbinol at $10^{-7}$-$10^{-4}$ mol/L enhanced insulin release ($p<0.05$-$p<0.01$) (EC50 of $1.5\times10^{-6}$ mol/L) at 5.6 mM basal glucose concentrations. At stimulatory glucose concentrations (16.7 mM glucose), Indole-3-carbinol enhanced insulin release at $10^{-6}$-$10^{-4}$ mol/L ($p<0.05$-$p<0.01$) (EC50 of $4.0\times10^{-7}$ mol/L). No cytotoxicity was observed.

[6]-gingerol at $10^{-8}$-$10^{-4}$ mol/L enhanced insulin release ($p<0.05$-$p<0.001$) (EC50 of $1.9\times10^{-6}$ mol/L) at 5.6 mM basal glucose concentrations. At stimulatory glucose concentrations (16.7 mM glucose), [6]-gingerol enhanced insulin release at $10^{-8}$-$10^{-4}$ mol/L ($p<0.05$-$p<0.001$) (EC50 of $2.8\times10^{-6}$ mol/L). No cytotoxicity was observed.

Medium chain fatty acids ($10^{-7}$-$10^{-4}$M) resulted in increased insulin secretion ($p<0.05$-$p<0.001$) with EC50 ranging from $4.5\times10^{-8}$ mol/L-$2.0\times10^{-5}$ mol/l at 5.6 mM glucose; and EC50 of $6.4\times10^{-8}$ mol/L-$1.3\times10^{-7}$ mol/L at 16.7 mM glucose.

All compositions of the present invention tested at 5.6 mM or 16.7 mM glucose resulted in no LDH release indicating no adverse effects on clonal BRIN-BD11 cells.

Example 3—Effect of Compositions of the Present Invention on Intracellular Ca2+ and cAMP in BRIN-BD11 Cells For confirmation of the stimulatory ability of compositions of the present invention on insulin secretion in pancreatic islets and to examine the mechanism of action, beta stimulus coupling pathways and changes in intracellular calcium concentrations and cAMP production in pancreatic BRIN-BD11 cells were examined.

At both basal and stimulatory glucose concentrations, compositions of the present invention ($10^{-4}$ mol/L) augmented intracellular Ca2+ concentrations at 5.6 mM glucose ($p<0.05$-$p<0.001$) (FIGS. 7-10) with the exception of Indole-3-carbinol and [6]-gingerol. At 16.7 mM glucose, Diindolylmethane, Embelin and [6]-shogaol increased intracellular Ca2+ concentrations ($p<0.001$) (FIG. 10).

As shown in FIG. 11, the stimulatory action of Diindolylmethane and Embelin on the insulin secretory pathway involves the cAMP-dependent pathway in pancreatic islets. [6]-shogaol and medium chain fatty acids act through the cAMP pathway.

Example 4—In Vivo Acute Effects of Compositions of the Present Invention on Plasma Glucose and Insulin in NIH Swiss Mice on Lean and High Fat Diet Administraton of compositions of the present invention resulted in a decrease in circulating glucose in vivo (FIG. 12). Diindolylmethane and Embelin decreased circulating glucose ($p<0.05$) in high fat fed mice. Plasma glucose was also significantly decreased ($p<0.001$) following administration of Indole-3-carbinol in high fat fed mice. [6]-gingerol also resulted in a significant decrease ($p<0.001$) in glucose in acute studies carried out in NIH Swiss mice.

The acute effects of medium chain fatty acids on plasma glucose were studied in NIH Swiss mice on normal chow and high fat diet following a glucose load (FIG. 13). The medium chain fatty acid ligands of GPR84 decreased plasma glucose after a glycaemic excursion ($p<0.001$) (FIG. 13).

Diindolylmethane ($p<0.01$) and Embelin ($p<0.01$) administration resulted in an increase in insulin release in high fat fed mice (FIG. 14).

Example 5—Long Term In Vivo Effects of Compositions of the Present Invention in NIH Swiss Mice on Lean and High Fat Diet Effects of Diindolylmethane and Embelin on food intake, fluid intake, body weight, non-fasting plasma glucose, insulin, glucagon and pancreatic insulin content were measured.

Embelin administration resulted in a significant decrease in plasma glucose in high fat fed mice after 9 days of treatment ($p<0.05$-$p<0.01$) (FIG. 15). Area under the curve results demonstrated a significant decrease ($p<0.05$, 17%) in plasma glucose over the 21 days.

Diindolylmethane administration resulted in a decrease in plasma glucose ($p<0.01$) at 21 days and area under the curve results demonstrated a significant decrease ($p<0.01$, 18% decrease) over the 21 day period.

Plasma insulin was augmented after 21 days by Embelin ($p<0.05$) and Diindolylmethane ($p<0.05$) (FIG. 16).

Daily oral administration of Embelin for 21 days had no effect on body weight while Diindolylmethane decreased body weight after 15 days (FIG. 17). Diindolylmethane decreased energy intake ($p<0.05$-$p<0.001$) (FIG. 18) and had no effect on fluid intake (FIG. 19).

Following long-term administration of Embelin, plasma glucose was significantly decreased ($p<0.001$), as demonstrated following a glucose load (FIG. 20). Plasma glucose was also attenuated by Diindolylmethane ($p<0.001$) (FIG. 20). Daily administration of Embelin ($p<0.001$) and Diindolylmethane ($p<0.001$) resulted in decreased plasma insulin (FIG. 21). Pancreatic insulin content was increased in the HFF mouse model (FIG. 22) due to islet size and insulin resistance. Embelin ($p<0.01$) and Diindolylmethane ($p<0.05$) reduced pancreatic insulin content in the HFF model (FIG. 22) which may have resulted in the decrease in circulating insulin. Insulin sensitivity was decreased with Embelin ($p<0.05$) and Diindolylmethane ($p<0.001$) (FIG. 23).

Interestingly, Diindolylmethane ($p<0.01$) and Embelin ($p<0.05$) increased GLP-1 secretion over the long term study, with a 61% and 45% increase in circulating GLP-1 at 30 min (FIG. 24). Plasma GLP-1 was raised in vivo by Diindolylmethane ($p<0.01$) and Embelin ($p<0.05$) at the end of the study (FIG. 25).

Embelin reduced total cholesterol ($p<0.05$) and low-density lipoprotein (LDL) cholesterol ($p<0.05$) in high fat fed mice (FIG. 26). Daily administration of Embelin resulted in no change in total body fat (FIG. 27) whilst Diindolylmethane decreased body fat ($p<0.01$) in high fat fed mice (FIG. 28).

Embelin and Diindolylmethane resulted in no change in body mineral density, bone mineral content and bone area in HFF mice (FIG. 29-30).

The present inventors have, for the first time, identified expression of GPR84 on pancreatic islets. This work has shown GPR84 distribution in pancreatic BRIN-BD11 cells and in mouse pancreatic tissue with GPR84 predominately co-expressed with insulin. This research has clearly demonstrated the expression of GPR84 in pancreatic islets and also, for the first time demonstrated the importance of GPR84 in islet cell function. In this study, the immunocytochemical cell work was complimented by studies demonstrating the effect of compositions of the present invention on insulin secretion in pancreatic islets. All compositions of the present invention exhibited enhanced potency in the clonal BRIN-BD11 cells and isolated mouse islets, and demonstrated that glucose sensitises insulin-secreting cells to the pharmacological actions of compositions of the present invention.

GPR84 has been shown in the use of the present invention to have an effect on the beta cell stimulus-secretion coupling pathway in pancreatic islets. The mechanism of action of GPR84 agonist-induced insulin release, examined intracellular Ca2+ and cAMP production in BRIN-BD11 cells. The compositions of the present invention caused a prompt augmentation in intracellular Ca2+, indicating modulation of insulin secretion is attributed partly through Ca2+ dependent pathways. In the use of the present invention, compositions of the present invention caused a moderate increase in total cAMP production, indicating that the compositions of the present invention predominately work through the Ca2+ activated pathway and to a lesser extent the cAMP dependent pathway.

The invention is not limited to the embodiment(s) described herein but can be amended or modified without departing from the scope of the present invention.

The invention claimed is:

1. A method of treating diabetes, the method comprising administering to a subject in need thereof (i) a pharmaceutical composition comprising an effective amount of embelin and (ii) glucose at a stimulatory concentration for enhancing insulin release.

2. The method of claim 1, wherein the pharmaceutical composition comprises a pharmaceutically acceptable amount of embelin.

3. The method of claim 1, wherein the pharmaceutical composition comprises from $10^{-12}$ to $10^{-4}$ mol/L of embelin.

4. The method of claim 1, wherein the pharmaceutical composition comprises $10^{-4}$ mol/L of embelin.

5. The method of claim 1, wherein said glucose at a stimulatory concentration is 16.7 mM glucose.

6. The method of claim 1, wherein the method comprises administering said glucose at a stimulatory concentration before the pharmaceutical composition comprising embelin.

7. The method of claim 1, wherein the method comprises co-administering said glucose at a stimulatory concentration with the pharmaceutical composition comprising embelin.

8. The method of claim 1, wherein the method comprises administering said glucose at a stimulatory concentration after the pharmaceutical composition comprising embelin.

9. The method of claim 1, wherein the pharmaceutical composition is administered in an amount such that the embelin is administered in an amount of 0.1 μmol/kg to 50 μmol/kg body weight of said subject.

10. The method of claim 1, wherein the pharmaceutical composition is administered in combination with said glucose in an amount such that the glucose is administered in an amount of 18 mmol/kg body weight of said subject.

* * * * *